United States Patent
Ferguson et al.

(10) Patent No.: US 12,429,487 B2
(45) Date of Patent: Sep. 30, 2025

(54) NEUROFILAMENT PROTEIN FOR GUIDING THERAPEUTIC INTERVENTION IN AMYOTROPHIC LATERAL SCLEROSIS

(71) Applicant: Biogen MA Inc., Cambridge, MA (US)

(72) Inventors: Toby Arlo Ferguson, Concord, MA (US); Danielle LeeZetta Graham, Concord, MA (US); Steve Sang-Woo Han, Needham, MA (US); Alexander Reid Vincent McCampbell, Andover, MA (US); Giulio Srubek-Tomassy, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 957 days.

(21) Appl. No.: 17/299,660

(22) PCT Filed: Dec. 3, 2019

(86) PCT No.: PCT/US2019/064190
§ 371 (c)(1),
(2) Date: Jun. 3, 2021

(87) PCT Pub. No.: WO2020/117772
PCT Pub. Date: Jun. 11, 2020

(65) Prior Publication Data
US 2022/0034907 A1 Feb. 3, 2022

Related U.S. Application Data

(60) Provisional application No. 62/842,063, filed on May 2, 2019, provisional application No. 62/840,431, filed
(Continued)

(51) Int. Cl.
*G01N 33/68* (2006.01)
*A61K 31/7115* (2006.01)
(Continued)

(52) U.S. Cl.
CPC ...... *G01N 33/6887* (2013.01); *A61K 31/7115* (2013.01); *A61P 25/28* (2018.01);
(Continued)

(58) Field of Classification Search
CPC ................ C12N 2310/11; A61K 31/7115
See application file for complete search history.

(56) References Cited

U.S. PATENT DOCUMENTS 8,465,727 B2 6/2013 Bowser
10,385,341 B2 8/2019 Swayze
(Continued)

FOREIGN PATENT DOCUMENTS

CN 104853778 8/2015
CN 106459972 2/2017
(Continued)

OTHER PUBLICATIONS

Breder, CD, and Kozauer, NA, Food and Drug Administration Center for Drug Evaluation and Research. Medical Review(s) Application No. 209176Orig1s000. Published May 2, 2017. (Year: 2017).*
(Continued)

*Primary Examiner* — Richard A Schnizer
*Assistant Examiner* — Africa M McLeod
(74) *Attorney, Agent, or Firm* — Choate, Hall & Stewart LLP; Stephanie L. Schonewald

(57) ABSTRACT

In one aspect, the invention provides a method for alleviating a symptom in a patient with amyotrophic lateral sclerosis, comprising administering an efficacious therapeutic that is efficacious to the patient, the efficacious therapeutic, when administered to the patient, resulting in a level of a neurofilament protein in a biological sample of the patient that is lower than a level of neurofilament protein in a patient with amyotrophic lateral sclerosis not administered the
(Continued)

therapeutic. In some embodiments, the patient is currently being administered with or has formerly been administered with either a non-efficacious therapeutic or a therapeutic that is different than the efficacious therapeutic.

12 Claims, 10 Drawing Sheets

Specification includes a Sequence Listing.

Related U.S. Application Data on Apr. 30, 2019, provisional application No. 62/776,253, filed on Dec. 6, 2018.

(51) Int. Cl.
 *A61P 25/28* (2006.01)
 *C12N 15/113* (2010.01)
(52) U.S. Cl.
 CPC ...... *C12N 15/1137* (2013.01); *C12N 2310/11* (2013.01); *C12N 2310/315* (2013.01); *C12N 2310/321* (2013.01); *C12N 2310/322* (2013.01); *C12N 2310/3341* (2013.01); *G01N 2800/28* (2013.01)

(56) References Cited

U.S. PATENT DOCUMENTS

| | | | |
|---|---|---|---|
| 10,669,546 | B2 | 6/2020 | Swayze |
| 10,968,453 | B2 | 4/2021 | Swayze |
| 11,474,113 | B2 | 10/2022 | Farwell |
| 2005/0019915 | A1 | 1/2005 | Bennett et al. |
| 2010/0267073 | A1 | 10/2010 | Przedborski et al. |
| 2015/0285822 | A1 | 10/2015 | Zhang et al. |
| 2017/0037410 | A1 | 2/2017 | Swayze |
| 2017/0087212 | A1 | 3/2017 | Passini et al. |
| 2017/0363643 | A1 | 12/2017 | Rigo et al. |
| 2019/0298708 | A1 | 10/2019 | Jain |
| 2020/0040342 | A1 | 2/2020 | Swayze |
| 2020/0239912 | A1 | 7/2020 | Sah |
| 2020/0354723 | A1 | 11/2020 | Swayze |
| 2021/0041459 | A1 | 2/2021 | Farwell |
| 2021/0172963 | A1 | 6/2021 | Benatar |
| 2022/0128578 | A1 | 4/2022 | Plavina |
| 2023/0107651 | A1 | 4/2023 | Farwell et al. |

FOREIGN PATENT DOCUMENTS

| | | | |
|---|---|---|---|
| CN | 107109407 | 8/2017 | |
| RU | 2655811 | 5/2018 | |
| WO | WO2007002390 | 1/2007 | |
| WO | WO2010129021 | 11/2010 | |
| WO | WO2010148249 | 12/2010 | |
| WO | WO2014110291 | 7/2014 | |
| WO | WO2015153800 | 10/2015 | |
| WO | WO-2015153800 A2 * | 10/2015 | ........... A61K 31/711 |
| WO | WO2015161170 | 10/2015 | |
| WO | WO2016040748 | 3/2016 | |
| WO | WO2018218219 | 11/2018 | |
| WO | WO2019147960 | 8/2019 | |
| WO | WO2020061355 | 3/2020 | |
| WO | WO2020117772 | 6/2020 | |
| WO | WO2020123783 | 6/2020 | |
| WO | WO2020167715 | 8/2020 | |

OTHER PUBLICATIONS

Rowland LP, Shneider NA. Amyotrophic lateral sclerosis. N Engl J Med. May 31, 2001;344(22):1688-700. doi: 10.1056/NEJM200105313442207. PMID: 11386269. (Year: 2001).*

Lu CH, et al. Neurofilament light chain: A prognostic biomarker in amyotrophic lateral sclerosis. Neurology. Jun. 2, 2015;84(22):2247-57. doi: 10.1212/WNL.0000000000001642. (Year: 2015).*

Benatar et al., "Neurofilament Light: A Candidate Biomarker of Presymtomatic Amyotrophic Lateral Sclerosis and Phenoconversion: Neurofilament Light in Presymptomatic ALS", Annals of Neurology, Jul. 2018, 84(1):130-139.

Daniela et al., CSF Neurofilament Proteins as Diagnostic and Prognostic Biomarkers for Amyotrophic Lateral Sclerosis, Journal of Neurology, Jan. 2018, 265(3):510-521.

Lu et al., "Neurofilament Light Chain: A Prognostic Biomarker in Amyotrophic Lateral Sclerosis", American Academy of Neurology, 2015, 84:2247-2257.

Lu et al., "Plasma Neurofilament Heavy Chain Levels Correlate to Markers of Late State Disease Progression and Treatment Response in SOD1G93A Mice that Model ALS", PLoS One, Jul. 2012, 7(7):e40998.

McCampbell et al., "Antisense Oligonucleotides Extend Survival and Reverse Decrement in Muscle Response in ALS Models", The Journal of Clinical Investigation, 2018, 128(8):3558-3567.

Puentes et al., "Immune Reactivity to Neurofilament Proteins in the Clinical Staging of Amytrophic Lateral Sclerosis", Journal Neurol. Neurosurg. Psychiatry, Sep. 2013, pp. 1-5.

Rosengren et al., "Patients with Amyotrohic Lateral Sclerosis and other Neurodegenerative Diseases have Increased Levels of Neurofilament Protein in CSF", Journal of Neurochemistry, Nov. 1996, 67(5):2013-2018.

Rossi, D. et al., CSF neurofilament proteins as diagnostic and prognostic biomarkers for amyotrophic lateral sclerosis, Journal of Neurology, 265(3):510-521 (2018).

Kharkevich, *Pharmacology*, 10th ed., GEOTAR Media, 2010-908 p., p. 73, 6 pages (with English Translation).

Verde et al., "Neurofilament light chain in serum for the diagnosis of amyotrophic lateral sclerosis," J. Neurol. Neurosurg. Psychiatry, Feb. 2018,90(2):157-164.

Bacioglu et al., "Correction: Update—Neurofilament Light Chain in Blood as CSF as Marker of Disease Progression in Mouse Models and in Neurodegenerative Diseases," Neuron, Jul. 20, 2016, 91(2):494-496.

Amor et al., "Neurofilament Light Antibodies in Serum Reflect Response to Natalizumab Treatment in Multiple Sclerosis", Multiple Sclerosis Journal, Sep. 2014, 20(10:1355-1362.

Bacioglu et al., "Neurofilament Light Chain in Blood CSF as Marker of Disease Progression in Mouse Models and in Neurodegenerative Diseases", Neuron, Jul. 2016, 91(1):56-66 Typo (marked).

Boido et al., "Neuromuscular Junctions as Key Contributors and Therapeutic Targets in Spinal Muscular Atrophy," Front Neuroanat, Feb. 3, 2016, 10(6):1-10.

Byme et al., "Neurofilament light protein in blood as a potential biomarker of neurodegeneration in Huntington's disease: a retrospective cohort analysis," Lancet Neuro., Aug. 2017, 16: 601-609.

Calabresi et al., "Serum Neurofilament Light (NFL): Towards a Blood Test for Prognosis and Disease/Treatment Monitoring in Multiple Sclerosis Patients", Neurology, Apr. 2018, 90(15):Supp. 1.

Chiriboga et al., "Nusinersen for the Treatment of Spinal Muscular Atrophy," Expert Rev Neurother, Sep. 8, 2017, 17(10):955-962.

Cifuentes-Diaz et al., "Neurofilament Accumulation at the Motor Endplate and Lack of Axonal Sprouting in a Spinal Muscular Atrophy Mouse Model", Human Molecular Genetics, Jun. 2002, 11(12): 1439-1447.

Costa et al., "Prognostic Value of Serum Neurofilaments with Clinically Isolated Syndromes", Neurology, Jan. 2019, 92(7):e733-e741 Typo (marked).

Costa et al., "Serum Neurofilament Light Chain Levels are Increased at the Onset of PML in Natalizumab Treated MS Patients" 70th Annual Meeting of the American Academy of Neurology, Apr. 2018, 1 page.

Costa et al., "Serum Neurofilament Light Chain Levels are Increased at the Onset of PML in Natalizumab-treated MS Patients", 4th Congress of the European-Academy-of-Neurology, Jun. 2018, p. 327.

Disanto et al., "Serum Neurofilament Light: A Biomarker of Neuronal Damage in Multiple Sclerosis: Serum NFL as a Biomarker in MS", Annals of Neurology, Jun. 2017, 81(6):857-870.

(56) References Cited

OTHER PUBLICATIONS

Fitzner et al., "Molecular Biomarkers in Cerebrospinal Fluid of Multiple Sclerosis Patients", Autoimmunity Reviews, Oct. 2015, 14(10):903-913.
Gunnarson et al., "Axonal Damage in Relapsing Multiple Sclerosis is Markedly Reduced by Natalizumab", Annals of Neurology, Jan. 2011, 69(1):83-89.
International Preliminary Report on Patentability in International Appln. No. PCT/US2019/015185, dated Aug. 6, 2020, 8 pages.
International Preliminary Report on Patentability in International Appln. No. PCT/US2019/051992, dated Apr. 1, 2021, 12 pages.
International Preliminary Report on Patentability in International Appln. No. PCT/US2020/017600, dated Aug. 26, 2021, 8 pages.
International Search Report and Written Opinion in International Appln. No. PCT/US2019/015185, dated Apr. 10, 2019, 16 pages.
International Search Report and Written Opinion in International Appln. No. PCT/US2019/051992, dated Jun. 24, 2020, 21 pages.
International Search Report and Written Opinion in International Appln. No. PCT/US2020/017600, dated May 26, 2020, 15 pages.
Khalil et al., "Neurofilaments as biomarkers in neurological disorders," Nature Reviews Neurology, Oct. 2018, 14:577-589.
Kiernan, "Progress towards therapy in motor neuron disease," Nature Reviews Neurology, Jan. 2018, 2 pages.
Kuhle et al., "Neurofilament Light and Heavy Subunits Compared as Therapeutic Biomarkers in Multiple Sclerosis," ACTA Neurologica Scandinavica, Dec. 2013, 128(6):E33-E36.
Linker et al., "Innovative Monoclonal Antibody Therapies in Multiple Sclerosis", Therapeutic Advances in Neurological Disorders, Jul. 2008, 1(1):33-42.
Novakova et al., "Monitoring Disease Activity in Multiple Sclerosis using Serum Neurofilament Light Protein", Neurology, Nov. 2017, 89(22):2230-2237.
Novakova et al., "Reduced Cerebrospinal Fluid Concentrations of Oxysterols in Response to Natalizumab Treatment of Relapsing Remitting Multiple Sclerosis", Journal of Neurological Sciences, Aug. 2015, 358(1):201-206.
Spinraza (nusinersen) injection, for intrathecal use, FDA, Label Dec. 2016, 13 pages.
Totzeck et al., "Neurofilament Heavy Chain and Tau Protein Are Not Elevated in Cerebrospinal Fluid of Adult Patients with Spinal Muscular Atrophy during Loading with Nusinersen," Int. J. Mol. Sci., Oct. 2019, 20(5397):1-10.
Weston et al., "Serum neurofilament light in familial Alzheimer disease," Neurology, Nov. 2017, 89:2167-2175.
Wurster et al., "Neurochemical Markers in CSF of Adolescent and Adult SMA Patients Undergoing Nusinersen Treatment", Therapeutic Advances in Neurological Disorders, May 2019, pp. 1-8.
Wurster et al., "Neurofilament Light Chain in Serum of Adolescent and Adult SMA Patients Under Treatment with Nusinersen", Journal of Neurology, 2020, 267:36-44.
Yuan et al., "Neurofilaments and Neurofilament Proteins in Health and Disease," Cold Spring Harb Persepct Biol., Apr. 2017, 9:a018309:1-24.
PCT International Search Report and Written Opinion in International Appln. No. PCT/US2019/064190, dated Mar. 4, 2020, 16 pages.

\* cited by examiner

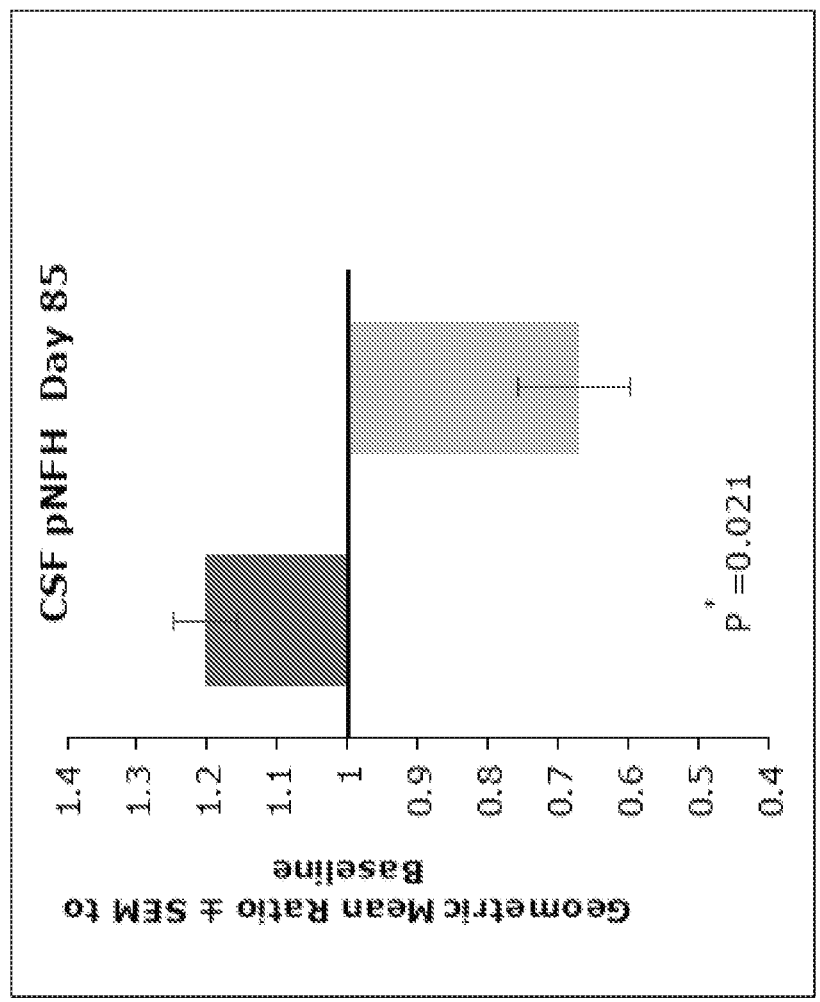

NEUROFILAMENT PROTEIN FOR GUIDING THERAPEUTIC INTERVENTION IN AMYOTROPHIC LATERAL SCLEROSIS

CROSS-REFERENCE TO RELATED APPLICATIONS

This application claims priority to U.S. Provisional Application No. 62/776,253, filed Dec. 6, 2018, U.S. Provisional Application No. 62/840,431, filed Apr. 30, 2019, and U.S. Provisional Application No. 62/842,063, filed May 2, 2019. The content of each of the foregoing applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 6, 2019, is named 13751-0312US1_SL.txt and is 45,057 bytes in size.

BACKGROUND OF THE INVENTION

The invention relates to the field of biology and medicine, and particularly to the field of amyotrophic lateral sclerosis (ALS). ALS (also known as motor neuron disease (MND), or Lou Gehrig's disease) is a progressive neurodegenerative disease that affects nerve cells in the brain and the spinal cord. The nerve cells affected in ALS are mainly those that are responsible for voluntary muscle movement, such as chewing, walking, and talking. Amyotrophic lateral sclerosis (ALS) is caused by the loss and dysfunction of neurons in motor pathways and leads to severe weakness, stiffness, and ultimately death in 3-5 years.

There are two different types of ALS, sporadic and familial. Sporadic, which is the most common form of the disease in the U.S., accounts for 90 to 95 percent of all cases. It may affect anyone, anywhere. Familial ALS (FALS) accounts for 5 to 10 percent of all cases in the U.S. Familial ALS means the disease is inherited. In those families, there is a 50% chance each offspring will inherit the gene mutation and may develop the disease. French neurologist Jean-Martin Charcot discovered the disease in 1869.

There is no known cure for ALS, but there are some therapeutics for alleviating the symptoms of ALS, including riluzole (marketed as Rilutek), edaravone (marketed as Radicava). Additional therapeutics, such as baclofen and diazepam, are used to control the spasticity caused by ALS, while trihexyphenidyl and glycopyrrolate can be used to help ALS patients who have trouble swallowing their saliva.

However, not every therapeutic alleviates symptoms in all ALS patients, and there is currently no known cure for ALS.

Thus, there remains a need for identifying new therapeutics that will alleviate the symptoms of ALS in patients.

BRIEF SUMMARY OF THE INVENTION

In some embodiments, the invention provides methods for identifying whether a therapeutic is efficacious for that patient and will thus alleviate one or more symptoms of ALS and slow down disability progression in that patient. In some embodiments, the invention provides methods of identifying a severe ALS disease early so an appropriate therapeutic is initiated as soon as possible. In some embodiments, the invention provides clinically-relevant cutpoints for specific context of use. In some embodiments, the invention provides methods to determine if an ALS patient is responding to an administered therapeutic (i.e., if the therapeutic is efficacious in that patient), and methods to treat an ALS patient with a therapeutic that will alleviate that patient's symptoms.

Accordingly, in a first aspect, the invention provides a method for alleviating symptoms in a patient with ALS, comprising administering an efficacious therapeutic that is efficacious to the patient, the efficacious therapeutic, when administered to the patient, resulting in a level of a neurofilament protein in a biological sample (e.g., blood, serum, plasma, or cerebral spinal fluid (CSF)) of the patient that is lower (e.g., at least 10%, 15%, 20%, 30%, 40%, 50%, 60%, 70%, 80%, 90%, or more, lower) than a level of neurofilament protein in a patient with ALS not administered the efficacious therapeutic. In some embodiments, the patient is currently being administered with or has formerly been administered with (a) a non-efficacious therapeutic or (b) a therapeutic that is different than the efficacious therapeutic.

In another aspect, the invention provides a method for determining if a therapeutic administered to a patient with ALS is efficacious to the patient, comprising obtaining or having obtained a biological sample (e.g., blood, serum, plasma, or cerebral spinal fluid (CSF)) from the patient administered with the therapeutic; and measuring or having measured a level of a neurofilament protein in a biological sample (e.g., blood, serum, plasma, or cerebral spinal fluid (CSF)) of the patient to obtain a post-treatment level, wherein a post-treatment level that is lower (e.g., at least 10%, 15%, 20%, 30%, 40%, 50%, 60%, 70%, 80%, 90%, or more, lower) than a level of neurofilament protein in a patient with ALS not administered the therapeutic identifies the therapeutic as being efficacious to the patient. In some embodiments, the patient is currently being administered with or has formerly been administered with (a) a non-efficacious therapeutic or (b) a therapeutic that is different than the efficacious therapeutic.

In another aspect, the invention provides a method for treating a patient with ALS with an efficacious therapeutic, comprising: (i) determining whether symptoms of ALS in the patient will be alleviated by a candidate therapeutic by: (a) obtaining or having obtained a biological sample (e.g., blood, serum, plasma, or cerebral spinal fluid (CSF)) from the patient following administration of the candidate therapeutic; and (b) measuring or having measured a level of a neurofilament protein in a biological sample (e.g., blood, serum, plasma, or cerebral spinal fluid (CSF)) of the patient to obtain a post-treatment level; and if the post-treatment level is lower (e.g., at least 10%, 15%, 20%, 30%, 40%, 50%, 60%, 70%, 80%, 90%, or more, lower) than a level of neurofilament protein in a patient with ALS not administered the candidate therapeutic, then the candidate therapeutic is an efficacious therapeutic and (ii) administering the efficacious therapeutic to the patient, wherein the efficacious therapeutic will alleviate the symptoms of ALS in the patient with ALS. In some embodiments, the patient is currently being administered with or has formerly been administered with (a) a non-efficacious therapeutic or (b) a therapeutic that is different than the candidate therapeutic.

In yet another aspect, the invention provides a method for identifying an efficacious therapeutic that will alleviate the symptoms of ALS in a patient with ALS, comprising administering a candidate therapeutic to the patient and measuring a level of a neurofilament protein in a biological sample (e.g., blood, serum, plasma, or cerebral spinal fluid (CSF)) of the treated patient after the patient has been administered for at least 5 weeks (e.g., at least 5, 6, 7, 8, 9, 10, 11, 12, 13, 14, 15, 16, 17, 18, 19, 20 weeks, or at least 1, 2, 3, 4, 5, 6, 7, 8, 9, 10, 11, or 12 months, or at least 1, 2, 3, years, or more) with the candidate therapeutic to obtain a post-treatment level, wherein a post-treatment level that is lower (e.g., at least 10%, 15%, 20%, 30%, 40%, 50%, 60%, 70%, 80%, 90%, or more, lower) than a level of neurofilament protein in a patient with ALS not administered the candidate therapeutic, identifies the candidate therapeutic as an efficacious therapeutic that will alleviate the symptoms of ALS in the patient. In some embodiments, the patient is currently being administered with or has formerly been administered with (a) a non-efficacious therapeutic or (b) a therapeutic that is different than the candidate therapeutic.

In various embodiments, the administration of the efficacious therapeutic slows the progression of the ALS disease in the patient.

In another aspect, the invention provides a method of treating amyotrophic lateral sclerosis in a human subject in need thereof, comprising: measuring a neurofilament protein level in a first biological sample obtained from the human subject; administering one or more doses of a therapeutic to the human subject; and measuring a neurofilament protein level in a second biological sample obtained from the human subject after administering the one or more doses of the therapeutic, wherein the neurofilament protein level in the second biological sample is lower than the neurofilament protein level in the first biological sample.

In some embodiments, the method entails administering further doses of the therapeutic to the human subject after measuring a neurofilament protein level in the second biological sample that is lower than the neurofilament protein level in the first biological sample.

In another aspect, the invention provides a method of treating amyotrophic lateral sclerosis in a human subject in need thereof, comprising: administering initial doses of a therapeutic to the human subject, wherein each of the initial doses is in the same amount and is administered at the same dosing interval between doses; measuring a neurofilament protein level in a first biological sample obtained from the human subject after administering the initial doses that is lower than a neurofilament protein level measured in a second biological sample obtained from the human subject prior to administering the initial doses; and administering further doses of the therapeutic to the human subject, wherein each of the further doses is in the same or lesser amount and at the same or lengthened dosing interval as compared to the initial doses.

In another aspect, the invention provides a method of treating amyotrophic lateral sclerosis in a human subject in need thereof, comprising: administering initial doses of a therapeutic to the human subject, wherein each of the initial doses is in the same amount and is administered at the same dosing interval between doses; measuring a neurofilament protein level in a first biological sample obtained from the human subject after administering the initial doses that is equal to or higher than a neurofilament protein level measured in a second biological sample obtained from the human subject prior to administering the initial doses; and administering further doses of the therapeutic to the human subject, wherein each of the further doses is in an increased amount and/or at a shortened dosing interval as compared to the initial doses.

In some embodiments of any of the foregoing methods, the therapeutic is an antisense compound according to the following formula:

mCes Aeo Ges Geo Aes Tds Ads mCds Ads Tds Tds Tds mCds Tds Ads mCeo Aes Geo mCes Te (nucleobase sequence of SEQ ID NO:8), wherein, A=an adenine,
mC=a 5-methylcytosine
G=a guanine,
T=a thymine,
e=a 2'-O-methoxyethylribose modified sugar,
d=in some embodiments, is a 2'-deoxyribose sugar,
s=a phosphorothioate internucleoside linkage, and
o=a phosphodiester internucleoside linkage;
or a pharmaceutically acceptable salt thereof.

In some embodiments of any of the foregoing methods, the patient or the human subject has a mutation in the superoxide dismutase 1 (SOD1) gene associated with amyotrophic lateral sclerosis. In some embodiments, the mutation in the SOD1 gene is A4V. In some embodiments, the mutation in the SOD1 gene is A4V, H46R, G93S, A4T, G141X, D133A, V148G, N139K, G85R, G93A, V14G, C6S, I113T, D49K, G37R, A89V, E100G, D90A, T137A, E100K, G41A, G41D, G41S, G13R, G72S, L8V, F20C, Q22L, H48R, T54R, S591, V87A, T88deltaTAD, A89T, V97M, S105deltaSL, V118L, D124G, L114F, D90A, G12R, or G147R.

In some embodiments of any of the foregoing methods, the neurofilament protein is a neurofilament light chain.

In some embodiments of any of the foregoing methods, the neurofilament protein is a neurofilament heavy chain (e.g., a phosphorylated neurofilament heavy chain).

In some embodiments of any of the foregoing methods, the first biological sample and the second biological sample comprise blood, serum, plasma, or cerebral spinal fluid.

BRIEF DESCRIPTION OF THE DRAWINGS

FIG. 6C is a graph showing the geometric mean ratio to baseline in CSF pNfH on day 85 in patients who were fast progressors treated with ASO1 100 mg versus placebo.

DETAILED DESCRIPTION

Figure 1:
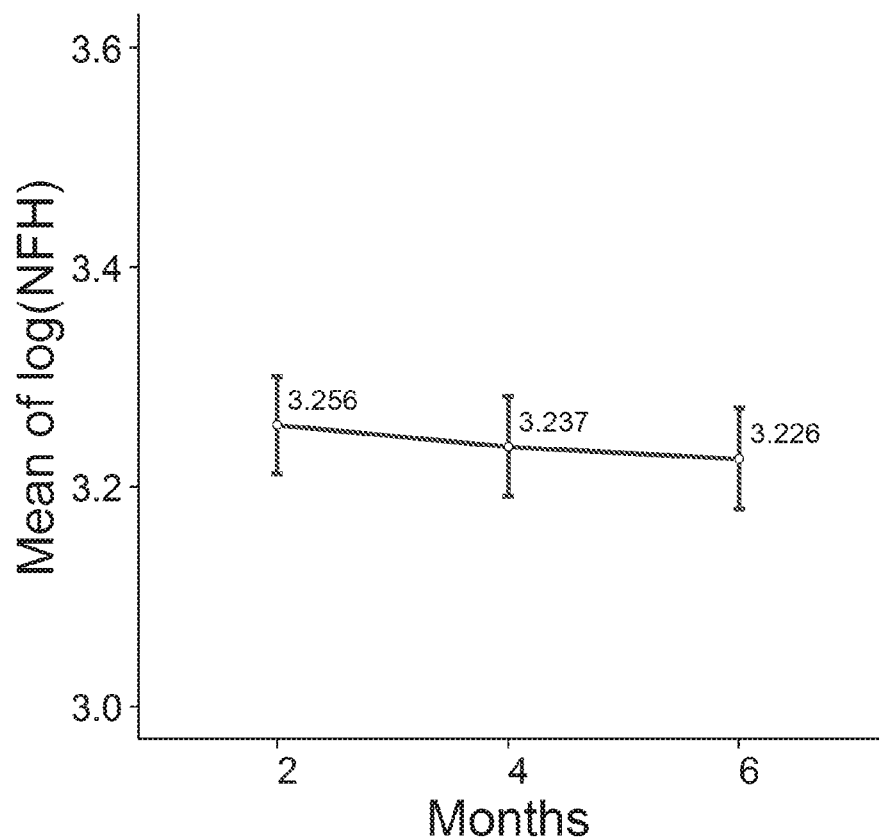
FIG. 1 is a line graph showing the longitudinal decline of plasma neurofilament heavy chain, with the mean decline being 1.8% per month.

In some embodiments, the invention provides methods to determine if an ALS patient will respond to a therapeutic, and methods to treat an ALS patient with a therapeutic that will alleviate that patient's symptoms. In some embodiments, the patient is a human.

The publications (including patent publications), web sites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

All amino acid sequences shown herein are in the amino (N) to carboxy (C) direction, unless indicated otherwise. All nucleotide sequences shown herein are in the 5' to 3' direction, unless indicated otherwise. When comprising or comprises is used in reference to an indicated amino acid sequence, it is meant that one or more amino acid residues can appear at the N' end of the indicated amino acid sequence, at the C' end of the indicated amino acid sequence, or at both end; but that one or more amino acid residues do not appear between stated amino acid residues in the indicated amino acid sequence. When comprising or comprises is used in reference to an indicated nucleotide sequence, it is meant that one or more nucleotide residues can appear at the 5' end of the indicated nucleotide sequence, at the 3' end of the indicated nucleotide sequence, or at both ends; but that one or more nucleotide residues do not appear between stated nucleotide residues in the indicated nucleotide sequence.

Terms defined or used in the description and the claims shall have the meanings indicated, unless context otherwise requires. Technical and scientific terms used herein have the meaning commonly understood by one of skill in the art to which the present invention pertains, unless otherwise defined. Any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

ALS is a progressive neurodegenerative disease that affects nerve cells in the brain and the spinal cord. In ALS, both upper motor neurons (motor neurons in the brain) and the lower motor neurons (motor neurons in the spinal cord and to motor nuclei of brain) degenerate or die, and stop sending messages to the muscles. Unable to function, the muscles gradually weaken, start to twitch (undergo fasciculations), and waste away (undergo atrophy). Eventually, the brain loses its ability to initiate and control voluntary movements. Decline is inevitable, with death, typically from respiratory failure, occurring 2 to 5 years, on average, following diagnosis. Although the majority of patients suffer from sporadic ALS, a smaller fraction of patients, approximately 2%, have an inherited, or familial, form of ALS caused by a variety of mutations in superoxide dismutase 1 (SOD1). Over 180 SOD1 mutations have been reported to cause this form of ALS (referred to as SOD1 ALS) since its initial discovery in 1993. The Amyotrophic Lateral Sclerosis Online Genetics Database (ALSoD). Institute of Psychiatry, Psychology & Neuroscience. Published 2015; Rosen, Nature, 364(6435):362 (1993)). Disease progression for individual mutations is variable, with survival of less than 15 months with the most severe mutations. Although the mechanism by which mutations cause SOD1 ALS is not known, compelling data suggest that toxic gain of function, not loss of SOD1 activity, is the trigger that initiates the cascade of events resulting in motor neuron death (Bruijn et al., Science, 281(5384):1851-4 (1998)).

The soluble SOD1 enzyme (also known as Cu/Zn superoxide dismutase) is one of the superoxide dismutases that provides defense against oxidative damage of biomolecules by catalyzing the dismutation of superoxide to hydrogen peroxide ($H_2O_2$) (Fridovich, Annu. Rev. Biochem., 64:97-112 (1995)). The superoxide anion ($O_2-$) is a potentially harmful cellular by-product produced primarily by errors of oxidative phosphorylation in mitochondria (Turrens, J. Physiol., 552:335-344 (2003)). Mutations in the SOD1 gene are associated with a dominantly-inherited form of ALS, a disorder characterized by a selective degeneration of upper and lower motor neurons (Rowland, N. Engl. J. Med., 2001, 344:1688-1700 (2001)). There is a tight genetic linkage between familial ALS and missense mutations in the SOD1 gene (Rosen, Nature, 362:59-62 (1993)). The toxicity of mutant SOD1 is believed to arise from an initial misfolding (gain of function) reducing nuclear protection from the active enzyme (loss of function in the nuclei), a process that may be involved in ALS pathogenesis (Sau, Hum. Mol. Genet., 16:1604-1618 (2007)). The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

Early symptoms of ALS usually include muscle weakness or stiffness. Gradually all muscles under voluntary control are affected, and individuals lose their strength and the ability to speak, eat, move, and even breathe. Most people with ALS die from respiratory failure, usually within 3 to 5 years from when the symptoms first appear. However, about 10 percent of people with ALS survive for 10 or more years.

There is no cure for ALS, and although there are therapeutics that are approved for administration to ALS patients, not every ALS patient will respond to every therapeutic. Thus, the treatment of ALS is challenging because not all ALS patients respond the same to the same therapeutic, and choosing the correct therapeutic for a particular patient can be difficult. Currently, it is up to a health care provider to select a particular therapeutic for use on a particular patient. The health care provider (e.g., physician) currently selects a particular therapeutic for treatment of a particular patient based on the alleviation of ALS symptoms in that particular patient, but there is no certainty that the particular therapeutic selected will, in fact, alleviate the symptoms of ALS in that particular patient.

To determine if a therapeutic alleviates the ALS symptoms in a particular patient, a therapeutic is judged by its ability to slow the progression of the ALS disease and/or reduce symptoms of ALS in a patient administered with the therapeutic as compared to a patient not administered with the therapeutic (e.g., an untreated patient or a patient prior to treatment).

Currently, symptoms in ALS is measured by functional tests such as muscle strength. One commonly used scale is the ALS Functional Rating Scale (ALSFRS or ALFRS-R). The ratings generally are based on categories such as speech, salivation, swallowing, handwriting, cutting food, dressing and hygiene, turning in bed, walking, climbing stairs, dyspnea, orthopnea, respiratory insufficiency. In some cases, the years since ALS diagnosis are taken into consideration. Each of the 12 categories is ranked by the patient on a scale of 0 to 4, with 0 being the worst (e.g., loss of speech in the speech category) and 4 being the best (e.g., normal speech in the speech category). From these factors, an ALSFRS-R rating can be calculated, with 0 being the worst (i.e., most afflicted) and 40 being the best (i.e., least symptomatic).

The Manual Muscle Test (MMT) can also be used on individual muscles, testing such measures as movement, contraction, range of motion, and ability to hold a position against pressure. The grading range is from 0-5 as follows:

Grade 0: No contraction or muscle movement.
Grade 1: Trace of contraction, but no movement at the joint.
Grade 2: Movement at the joint with gravity eliminated.
Grade 3: Movement against gravity, but not against added resistance.
Grade 4: Movement against external resistance with less strength than usual.
Grade 5: Normal strength.

In some embodiments, a therapeutic is said to alleviate the symptoms of ALS in a particular patient (i.e., be efficacious in that patient) if, after administration of the therapeutic for at least three months, the ALSFRS-R score of the patient stays the same, increases, or decreases by 1.0 or less as compared to the patient's ALSFRS-R score prior to start of administration of the therapeutic. For example, a therapeutic is said to alleviate the symptoms of ALS if, prior to administration, the patient had an initial ALSFRS-R score of 20 and after three months of treatment with the therapeutic, the patient's ALSFRS-R score remains 20 or increases (e.g. to 25 or 30) or decreases to 19. In some embodiments, a therapeutic is said to alleviate the symptoms of ALS if, after administration of the therapeutic for at least six months, the ALSFRS-R score of the patient stays the same, increases, or decreases by 1.0 or less as compared to the patient's ALSFRS-R score prior to start of administration of the therapeutic. In some embodiments, a therapeutic is said to alleviate the symptoms of ALS if, after administration of the therapeutic for at least twelve months, the ALSFRS-R score of the patient stays the same, increases, or decreases by 1.0 or less as compared to the patient's ALSFRS-R score prior to start of administration of the therapeutic.

Another functional test that can be used to assess ALS symptoms and their severity is the slow vital capacity (SVC) test. The SVC is a spirometry test that displays the volume of gas measured. on a low complete expiration after a maximal inspiration without forced or rapid effort.

An additional functional test that can be used to assess ALS symptoms and their severity are the hand-held dynamometry (HHD) test.

Although the functional tests such as the ALSFRS-R test are non-invasive, they are time consuming to administer, often show changes only after months and sometimes years. Moreover, once function declines, it may be difficult to regain it. Thus, disease progression of ALS can also be detected by keeping track of physical changes, preferably before evidence of functional decline.

Thus, there is a need to find a way to identify a therapeutic will be efficacious in a particular patient that is not based on loss of function that has already occurred prior to administering the functional test.

Neurofilaments (NF) are proteins found in the cytoplasm of neurons. They are protein polymers measuring approximately 10 nm in diameter and many micrometers in length. Together with microtubules and microfilaments, they form the neuronal cytoskeleton. Neurofilaments are composed of different proteins including neurofilament protein L (low molecular weight, NFL, also called neurofilament light chain), neurofilament protein M (medium molecular weight; NFM, also called neurofilament medium chain) and neurofilament protein H (high molecular weight; NFH, also called neurofilament heavy chain). Neurofilaments in the mammalian nervous system also contain the protein internexin and that neurofilaments in the peripheral nervous system can also contain the protein peripherin.

Thus, as used herein, "a neurofilament protein" is meant neurofilament protein L (low molecular weight, NFL, also called neurofilament light chain), neurofilament protein M (medium molecular weight; NFM, also called neurofilament medium chain), neurofilament protein H (high molecular weight; NFH, also called neurofilament heavy chain), internexin and peripherin. The amino acid sequence of human neurofilament light chain is provided in SEQ ID NO:1 and in Julien et al., Biochimica et Biophysica Acta 909: 10-20, 1987 (see also NCBI Reference Sequence: NP_006149.2 and NCBI Reference Sequence: NG_008492.1). The amino acid sequences of human neurofilament heavy chain are provided in SEQ ID NO:2 and SEQ ID NO:3, and in Lees et al., EMBO J. 7(7): 1947-1955, 1988 (see also NCBI Reference Sequence: NG_008404.1 and NCBI Reference Sequence: NP_066554.2). The amino acid sequences of human neurofilament medium chain are provided in SEQ ID NO:4 and SEQ ID NO:5 and in Myers et al., EMBO J. 6(6): 1617-1626, 1987. SEQ ID NO:6 provides the sequence of human internexin protein. SEQ ID NO:7 provides the sequence of human peripherin protein.

Because of their specific structural role in neurons, neurofilaments can be used to assess neuron integrity. When a neuron is damaged, neurofilament escapes the damaged neuron and can be found in cerebral spinal fluid (CSF) or even in blood (e.g., in the serum or plasma component of the blood). Patients with neurodegenerative diseases manifest elevated levels of neurofilaments in cerebrospinal fluid and plasma (see Yuan A, et al. Cold Spring Harb Perspect Biol. 2017; 9(4). 2. Weydt P, et al. Ann Neurol 2016; 79(1):152-158). This may represent extracellular release of the axonal contents of degenerating neurons. Indeed, in observational and largely cross-sectional data from patients with amyotrophic lateral sclerosis (ALS), correlations have been demonstrated between neurofilament levels and disease severity, as indicated by rates of survival and decline in Amyotrophic Lateral Sclerosis Functional Rating Scale-Revised (ALSFRS-R) (see McCombe P A, et al. J Neurol Sci. 2015; 353(1-2):122-129; Boylan K B, et al. Neurol Neurosurg Psychiatry. 2013; 84(4):467-472).

In some embodiments, the neurofilament protein is a neurofilament light chain. In some embodiments, the neurofilament light chain is phosphorylated. Assays for measuring neurofilament light chain in serum has been described (see, e.g., Gaiottino et al., PLoS ONE 8: e75091, 2013; Kuhle et al., J. Neurol. Neurosurg. Psychiatry 86(3): 273-279, 2014. For example, blood serum from the patient centrifuged at 1000 g for 10 minutes at room temperature and stored at −80° C. within 2 hours of collection. Neurofilament light chain (NfL) (e.g., serum NfL) concentrations can be measured (e.g., in duplicate) using ready-to-use enzyme linked immunosorbent assay (ELISA) diluent; Mabtech AB, Nacka Strand, Sweden) or an electrochemiluminescence (ECL) immunoassay described in Gaiottino et al., PLoS ONE 8: e75091, 2013, or a single molecule array (SIMOA) method described in Disanto et al., Ann. Neurol. 81(6): 857-870, 2017. The three assay methods have been compared in Kuhl et al., Clinical Chemistry and Laboratory Medicine 54 (10): 1655-1661, 2016. The SIMOA assay (particularly called the Simoa NF-light Advantage kit) is commercially available from Quanterix Corp. (Lexington, MA, USA).

The medium chain and/or heavy chain of neurofilament protein can also be measured in according with some embodiments of the invention.

For example, the SimplePlex platform can be used to measure the levels of phosphorylated Nf heavy chain (pNf-H). SimplePlex is commercially available from Protein Simple (San Jose, CA, USA) (See Dysinger M, et al. *J Immunol Methods.* 451:1-10, 2017). In some embodiments, the neurofilament heavy chain is phosphorylated.

Although elevated neurofilament light chain levels in the CSF and serum have been described as correlating with physical damage as observed with MRI, as described herein, the inventors have discovered that elevated (or increased) levels of neurofilament protein in the serum and/or CSF can predict future physical damage or functional loss in an ALS patient. Thus, by keeping track of the level of a neurofilament protein in the serum (or CSF) of a patient on a particular therapeutic, a health care provider can predict whether the patient is responding to the therapeutic (i.e., whether the therapeutic alleviates the symptoms in that patient) before the patient shows functional loss and/or physical damage.

In one aspect, the invention provides a method for alleviating ALS symptoms in a patient with ALS, comprising administering a therapeutic that maintains or reduces the level of a neurofilament protein in a biological sample (e.g., blood, serum, plasma, or cerebral spinal fluid (CSF)) of the patient as compared to the level of the neurofilament protein in a biological sample (e.g., blood, serum, plasma, or cerebral spinal fluid (CSF)) of (a) a patient not administered with the therapeutic or (b) the patient prior to administration of the therapeutic.

In another aspect, the invention provides a method to determine if a candidate therapeutic will be efficacious in a particular patient and thus useful for alleviating the symptoms of ALS disease in that patient by determining if the candidate therapeutic is able to reduce the level of neurofilament protein (e.g., serum or CSF neurofilament protein) in the patient, as compared to the level in the patient prior to treatment with that candidate therapeutic. If the candidate therapeutic is able to reduce the level of neurofilament protein (e.g., serum or CSF neurofilament) in the patient as compared to the level in the patient prior to treatment with the candidate therapeutic, that candidate therapeutic is identified as being efficacious in that patient.

In another aspect, the invention provides a method for alleviating symptoms in a patient with ALS, comprising administering an efficacious therapeutic that is efficacious to the patient, the efficacious therapeutic, when administered to the patient, resulting in a level of a neurofilament protein in serum of the patient that is lower than an amount equivalent to 16 pg serum neurofilament light chain per ml serum or lower than a level of neurofilament protein in a patient with amyotrophic lateral sclerosis not administered the therapeutic. In some embodiments, the patient is currently being administered with or has formerly been administered with either a non-efficacious therapeutic or a therapeutic that is different than the efficacious therapeutic.

In some embodiments, the neurofilament protein is a neurofilament light chain (NfL). In some embodiments, the neurofilament protein is a neurofilament medium chain (NfM). In some embodiments, the neurofilament protein is a neurofilament heavy chain (NfH) (e.g., a phosphorylated neurofilament heavy chain (pNfH)). In some embodiments, the neurofilament protein is a human protein. In some embodiments, the level (i.e., amount or quantity) of neurofilament protein in a biological sample (e.g., blood, serum, plasma, or cerebral spinal fluid (CSF)) is measured.

It will be understood that when a level of a neurofilament protein (e.g., a neurofilament protein described herein, e.g., NfL or NfH, e.g., pNfH) is described as being increased (i.e., raised), the same as (or equal to), or decreased (i.e., reduced), that level is being compared to a level obtained with the same assay method from the same type of fluid. For example, an after-treatment level of serum neurofilament light chain (sNfL) obtained from a patient's serum using the Simoa assay will be compared with a baseline (i.e., before start of treatment) level of sNfL from the patient using the Simoa assay or will be compared to the level of sNfL as measured by the Simoa assay in serum of a patient that is not being treated. It will also be understood that the "level" of a neurofilament protein can be described in any matter, for example, in picograms of a neurofilament protein (e.g., neurofilament light chain) per mL of a biological sample (e.g., blood, serum, plasma, or cerebral spinal fluid (CSF)).

By "therapeutic" is simply meant a drug or agent that may be used to treat amyotrophic lateral sclerosis. The therapeutic need not actually cure the disease, and there is currently no known cure for amyotrophic lateral sclerosis. Thus, a patient being "treated" with a therapeutic simply means that he/she is being administered a therapeutic that might be efficacious for his or her disease. The therapeutic may not be efficacious in all ALS patients. Rather, therapeutics for ALS are sometimes referred to as disease-modifying therapies or disease-modifying drugs, (DMTs or DMDs), because their administration reduces the symptoms of ALS in some patients, and thus allow those patients with ALS who respond to the therapeutic to have an improved quality of life and/or improved neuromuscular function. Current therapeutics, if efficacious, slow the progression of the ALS disease and/or alleviate symptoms in the responding patients.

Thus, by "efficacious" is meant that a therapeutic will reduce the symptoms of an ALS patient.

In the US, there are two therapeutics approved by the U.S. Food and Drug Administration to treat ALS.

The first, riluzole (sold as Rilutek; Condordia), is administered as an orally ingestible pill and appears to slow the disease's progression in some people with ALS. Although its exact mechanism is unknown, it may reduce levels of glutamate in the brain, since glutamate is often present in higher levels in people with ALS. However, administration of riluzole may cause side effects such as dizziness, gastrointestinal conditions and liver function changes.

The second FDA approved therapeutic, edaravone (sold as Radicava; Mitsubishi), was approved after evidence from a clinical trial showed that its administration over a six month period resulted in a reduction the decline in daily functioning associated with ALS. Side effects of edaravone (which is administered intravenously) include bruising, gait disturbance, hives, swelling and shortness of breath.

Additional new types of therapeutics for treating ALS and/or alleviating ALS symptoms that are still in development and/or are approved outside of the US include, without limitation, Neuronata-R (Corestem), KPT-350 (Biogen/Karyopharm Therapeutics), CNS10-NPC-GDNF (Svedsen Lab), Cu(II)ATSM (ProCypra Therapeutics), BIIB067 targeting levels of the SOD1 protein (Biogen/Ionis), GM604 (Genervon Biopharmaceuticals), an ASO described herein (e.g., ASO1, ASO2, or ASO3), and an ASO described in US 2017/0037410A1, incorporated herein by reference in its entirety.

In some embodiments, a therapeutic, e.g., a candidate and/or efficacious ALS therapeutic, comprises a small molecule, an antibody or fragment thereof, a nucleic acid molecule (e.g., antisense oligonucleotide, a microRNA, an aptamer, a short hairpin RNA, or a small interfering RNA), a mesenchymal stem cell, a glial restricted progenitor cell, and/or a viral vector (e.g., adenovirus or adeno-associated virus). In some embodiments, the viral vector comprises or encodes one or more of: an antibody or fragment thereof, and/or a nucleic acid molecule (e.g., antisense oligonucleotide, microRNA, aptamer, short hairpin RNA, or small interfering RNA).

In some embodiments, the therapeutic targets one or more genetic mutation(s) associated with ALS. In some embodiments, a therapeutic, e.g., a candidate and/or efficacious ALS therapeutic, comprises a molecule that targets (e.g., binds, degrades, and/or decreases the levels of) a SOD1 gene (e.g., a mutated SOD1 gene), a SOD1 RNA (e.g., a mutated SOD1 RNA), and/or a SOD1 polypeptide (e.g., a mutated SOD1 polypeptide). In embodiments, a mutated SOD1 gene, RNA, or polypeptide is associated with ALS. In embodiments, a therapeutic comprises a microRNA against SOD1, e.g., VY-SOD101 (Voyager Therapeutics). In some embodiments, a therapeutic, e.g., a candidate and/or efficacious ALS therapeutic, comprises a nucleic acid targeting SOD1 as described in US2018282732A1, incorporated herein by reference in its entirety. In some embodiments, a therapeutic comprises an antisense oligonucleotide that targets a SOD1 gene (e.g., a mutated SOD1 gene).

In some embodiments, a therapeutic, e.g., a candidate and/or efficacious ALS therapeutic, comprises a molecule that targets (e.g., binds, degrades, and/or decreases the levels of) a chromosome 9 open reading frame 72 (C9orf72) hexanucleotide expansion polynucleotide (e.g., DNA or RNA), and/or a C9ORF72 dipeptide repeat (DPR) polypeptide. In some embodiments, the therapeutic comprises a microRNA that targets C9orf72, e.g., as described in Martier et al. Mol. Therapy Nuc. Acids 14(2019):P593-608.

In some embodiments, a therapeutic, e.g., a candidate and/or efficacious ALS therapeutic, comprises one or more of: riluzole, edaravone, copper-ATSM, masitinib, tirasemtiv, NP001, pyrimethamine, mecobalamin, ibudilast, mexiletine, GDC-0134, memantine, EPI-589, tocilizumab, RNS-60, pimozide, ODM-109, ezogabine, amylyx, or low-dose IL-2. In some embodiments, a therapeutic, e.g., a candidate and/or efficacious ALS therapeutic, comprises an antisense oligonucleotide comprising one or more of: an anti-C9orf72 antisense oligonucleotide (e.g., as described in Sareen et al. Sci. Transl. Med. 2013; 5(208):208ra149); BIIB067 (e.g., as described in Clinical Trials Identifier No. NCT02623699); AS0816 (e.g., as described in Sareen et al. Sci. Transl Med. 2013; 5(208):208ra149); ISIS SMNRx, ISIS 333611 (e.g., as described in Miller et al. Lancet Neurol. 2013; 12(5):435-42); or AS0061 (e.g., as described in Sareen et al. Sci. Transl. Med. 2013; 5(208):208ra149).

In some embodiments, a therapeutic, e.g., a candidate and/or efficacious ALS therapeutic, comprises one or more of: Betamethasone (e.g., as described in ClinicalTrials.gov Identifier: NCT03707795); MCI-186 (e.g., as described in ClinicalTrials.gov Identifier: NCT01492686); ONO-2506PO (e.g., as described in ClinicalTrials.gov Identifier: NCT00694941); TRO19622 NCT01285583; E0302 (e.g., as described in ClinicalTrials.gov Identifier: NCT00444613); AP-101 (e.g., as described in ClinicalTrials.gov Identifier: NCT03981536); Rasagiline (e.g., as described in ClinicalTrials.gov Identifier: NCT01232738); TCH346 (e.g., as described in ClinicalTrials.gov Identifier: NCT00230074); NP001 (e.g., as described in ClinicalTrials.gov Identifier: NCT01281631); Triumeq (e.g., as described in ClinicalTrials.gov Identifier: NCT02868580); Masitinib (e.g., as described in ClinicalTrials.gov Identifier: NCT02588677); Granulocyte Colony Stimulating Factor (e.g., as described in ClinicalTrials.gov Identifier: NCT01825551); CK-2127107 (e.g., as described in ClinicalTrials.gov Identifier: NCT03160898); Tirasemtiv (e.g., as described in ClinicalTrials.gov Identifier: NCT02936635); Gilenya (e.g., as described in ClinicalTrials.gov Identifier: NCT01786174); Arimoclomol (e.g., as described in ClinicalTrials.gov Identifier: NCT00706147); Pimozide (e.g., as described in ClinicalTrials.gov Identifier: NCT03272503); Nuedexta (e.g., as described in ClinicalTrials.gov Identifier: NCT01806857); KNS-760704 (e.g., as described in ClinicalTrials.gov Identifier: NCT00931944); MN-166 (e.g., as described in ClinicalTrials.gov Identifier: NCT04057898); SB-509 (e.g., as described in ClinicalTrials.gov Identifier: NCT00748501); KNS-760704 (e.g., as described in ClinicalTrials.gov Identifier: NCT00647296); Olesoxime (e.g., as described in ClinicalTrials.gov Identifier: NCT00868166); Levosimendan (e.g., as described in ClinicalTrials.gov Identifier: NCT03505021); Memantine (e.g., as described in ClinicalTrials.gov Identifier: NCT00353665); BIIB067 (e.g., as described in ClinicalTrials.gov Identifier: NCT02623699); BIIB078 (e.g., as described in ClinicalTrials.gov Identifier: NCT03626012); or BIIB100 (e.g., as described in ClinicalTrials.gov Identifier: NCT03945279).

In some embodiments, a therapeutic, e.g., a candidate and/or efficacious ALS therapeutic, comprises an antisense oligonucleotide, e.g., as described in WO2019032607A1; WO 2015/153800; WO 2003/000707; WO 2014/062691; WO 2015/054676; WO 2016/168592; WO 2014/062686; WO 2014/062736; WO 2017/079291; WO 2017/180835; WO 2015/057727; WO 2015/057738; WO 2016/112132; WO 2016/167780; WO 2015/143246; WO 2015/143245; WO 2017/117496, each of which are incorporated herein by reference in their entirety.

In some embodiments, a therapeutic, e.g., a candidate and/or efficacious ALS therapeutic, comprises a small molecule, e.g., as described in WO 2013/170068, incorporated herein by reference in its entirety.

In some embodiments, a therapeutic, e.g., a candidate and/or efficacious ALS therapeutic, comprises a polypeptide, e.g., antibody or fragment thereof, e.g., as described in WO 2016/050822 and WO 2019/210054, both of which are incorporated herein by reference in their entireties. In some embodiments, a therapeutic, e.g., a candidate and/or efficacious ALS therapeutic, comprises an antibody or fragment thereof comprising a variable heavy chain amino acid sequence, a variable light chain amino acid sequence, and/or the complementarity determining regions (CDRs) of one of the following antibodies: NI-308.18F7, NI-308.1507, NI-308.28G1, NI-308.45C2, NI.308.24E11, NI-308.5G2, NI-308.46E9, N1308-6B11, NI-308.46F8, NI-308.4M1, NI-308.12A3, or NI-308.16C10, as described in WO 2016/050822, incorporated herein by reference. In some embodiments, a therapeutic, e.g., a candidate and/or efficacious ALS therapeutic, comprises an antibody or fragment thereof comprising a variable heavy chain amino acid sequence, a variable light chain amino acid sequence, and/or the complementarity determining regions (CDRs) chosen from SEQ ID Nos: 40, 44, 45, 46, 47, 48, 49, and/or 50 as described in WO 2019/210054, and/or a sequence in Table 14 of WO 2019/210054, incorporated herein by reference.

By "administration" or "administering" is meant delivery of a therapeutic to a patient. The route of administration can be by any means including, without limitation, oral, rectal, intravenous, intrathecal, intraperitoneal, intramuscular, subcutaneous, nasal, topical, parenteral, and sublingual. The dosage amount and dosing schedule for a therapeutic can be according to the label of the regulatory agency (e.g., the U.S. Food and Drug Administration or the European Medicines Agency). A patient who is administered a therapeutic may be referred to as being treated with that therapeutic, regardless of if the patient actually responds to the administered therapeutic. If a patient does not respond to an administered therapeutic, that therapeutic is non-efficacious in that patient.

By "symptoms of ALS" is meant any of the symptoms that a patient with ALS may experience. Symptoms of ALS include, without limitation, muscle weakness, problems with coordination, stiff muscles, loss of muscle, muscle spasms, overactive reflexes, difficulty speaking, vocal cord spasms, difficulty swallowing, drooling, lack of restraint, mild cognitive impairment, severe constipation, severe unintentional weight loss, shortness of breath, difficulty raising the foot, and other symptoms that individuals with amyotrophic lateral sclerosis experience. For the avoidance of doubt, neurofilament protein (e.g., neurofilament light chain or neurofilament heavy chain) in the biological sample (e.g., blood, serum, plasma, or cerebral spinal fluid (CSF)) is not a symptom of ALS. Therefore, a therapeutic that simply reduces a neurofilament protein in the biological sample (e.g., blood, serum, plasma, or cerebral spinal fluid (CSF)) without reducing any symptoms of ALS in an ALS patient is non-efficacious in that patient.

As used herein, by "alleviate the symptoms of ALS" is meant that a therapeutic will reduce ALS disease symptoms in a patient and/or slow the progression of the ALS disease. A patient whose ALS symptoms are alleviated by being administered a therapeutic is said to respond to, or to be responsive to, the indicated therapeutic. For example, a therapeutic that alleviates the symptoms of ALS in the patient will, upon administration of the therapeutic, result in an ALS Functional Rating Scale (ALSFRS or ALFRS-R) rating that is the same as or higher than, or less than 1.0 lower than an ALS patient not treated with the therapeutic or than the ALS patient prior to treatment with the therapeutic. If a therapeutic is able to alleviate the symptoms of ALS upon administration of the therapeutic to that patient, the therapeutic is referred to as being efficacious in that patient.

It should be noted that reference to a patient "not being administered the therapeutic" is simply a patient (e.g., an ALS patient) who has not been treated with the indicated therapeutic. Thus, this patient may be the same patient that is, at some future point in time, administered the indicated therapeutic, or this might be a completely different patient who is not being administered the indicated therapeutic. Note that the patient not being administered the therapeutic might be currently being treated with another therapeutic, or may have been treated with the indicated therapeutic in the past, but is not currently being treated with the indicated therapeutic.

In some embodiments, the maintenance or reduction of the level of a neurofilament protein (e.g., neurofilament light chain) in the biological sample (e.g., blood, serum, plasma, or cerebral spinal fluid (CSF)) of a patient that will have his or her ALS symptoms alleviated by the therapeutic (as compared to the level of the untreated patient) is detectable at least two months, 2.5 months, three months, four months, five months, or at least six months, or at least one year prior to observation of alleviation of ALS symptoms (as determined by one of the assessments described herein).

```
Sequence Disclosure
(human neurofilament light chain amino acid sequence)
                                                       SEQ ID NO: 1
MSSFSYEPYYSTSYKRRYVETPRVHISSVRSGYSTARSAYSSYSAPVSSSLSVRRSYSSSSGSLMPSLEN

LDLSQVAAISNDLKSIRTQEKAQLQDLNDRFASFIERVHELEQQNKVLEAELLVLRQKHSEPSRFRALY

E

QEIRDLRLAAEDATNEKQALQGEREGLEETLRNLQARYEEEVLSREDAEGRLMEARKGADEAALARA

ELE

KRIDSLMDEISFLKKVHEEEIAELQAQIQYAQISVEMDVTKPDLSAALKDIRAQYEKLAAKNMQNAEE

WF

KSRFTVLTESAAKNTDAVRAAKDEVSESRRLLKAKTLEIEACRGMNEALEKQLQELEDKQNADISAMQ

DT

INKLENELRTTKSEMARYLKEYQDLLNVKMALDIEIAAYRKLLEGEETRLSFTSVGSITSGYSQSSQVFG

RSAYGGLQTSSYLMSTRSFPSYYTSHVQEEQIEVEETIEAAKAEEAKDEPPSEGEAEEEEKDKEEAEEEE

AAEEEEAAKEESEEAKEEEGGEGEEGEETKEAEEEEKKVEGAGEEQAAKKKD
```

-continued (human neurofilament heavy chain amino acid sequence)
SEQ ID NO: 2

MMSFGGADALLGAPFAPLHGGGSLHYALARKGGAGGTRSAAGSSSGFHSWTRTSVSSVSA

SPSRFRGAGAASSTDSLDTLSNGPEGCMVAVATSRSEKEQLQALNDRFAGYIDKVRQLEA

HNRSLEGEAAALRQQQAGRSAMGELYEREVREMRGAVLRLGAARGQLRLEQEHLLEDIAH

VRQRLDDEARQREEAEAAARALARFAQEAEAARVDLQKKAQALQEECGYLRRHHQEEVGE

LLGQIQGSGAAQAQMQAETRDALKCDVTSALREIRAQLEGHAVQSTLQSEEWFRVRLDRL

SEAAKVNTDAMRSAQEEITEYRRQLQARTTELEALKSTKDSLERQRSELEDRHQADIASY

QEAIQQLDAELRNTKWEMAAQLREYQDLLNVKMALDIEIAAYRKLLEGEECRIGFGPIPF

SLPEGLPKIPSVSTHIKVKSEEKIKVVEKSEKETVIVEEQTEETQVTEEVTEEEEKEAKE

EEGKEEEGGEEEEAEGGEEETKSPPAEEAASPEKEAKSPVKEEAKSPAEAKSPEKEEAKS

PAEVKSPEKAKSPAKEEAKSPPEAKSPEKEEAKSPAEVKSPEKAKSPAKEEAKSPAEAKS

PEKAKSPVKEEAKSPAEAKSPVKEEAKSPAEVKSPEKAKSPTKEEAKSPEKAKSPEKAKS

PEKEEAKSPEKAKSPVKAEAKSPEKAKSPVKAEAKSPEKAKSPVKEEAKSPEKAKSPVKE

EAKSPEKAKSPVKEEAKTPEKAKSPVKEEAKSPEKAKSPEKAKTLDVKSPEAKTPAKEEA

RSPADKFPEKAKSPVKEEVKSPEKAKSPLKEDAKAPEKEIPKKEEVKSPVKEEEKPQEVK

VKEPPKKAEEEKAPATPKTEEKKDSKKEEAPKKEAPKPKVEEKKEPAVEKPKESKVEAKK

EEAEDKKKVPTPEKEAPAKVEVKEDAKPKEKTEVAKKEPDDAKAKEPSKPAEKKEAAPEK

KDTKEEKAKKPEEKPKTEAKAKEDDKTLSKEPSKPKAEKAEKSSSTDQKDSKPPEKATED

KAAKGK

SEQ ID NO: 3
  1 mmsfggadal lgapfaplhg ggslhyalar kggaggtrsa agsssgfhsw trtsvssvsa
 61 spsrfrgaga asstdsldtl sngpegcmva vatsrsekeq lqalndrfag yidkvrqlea
121 hnrslegeaa alrqqqagrs amgelyerev remrgavlrl gaargqlrle qehllediah
181 vrqrlddear qreeaeaaar alarfaqeae aarvdlqkka qalqeecgyl rrhhqeevge
241 llgqiqgsga aqaqmqaetr dalkcdvtsa lreiraqleg havqstlqse ewfrvrldrl
301 seaakvntda mrsaqeeite yrrqlqartt elealkstkd slerqrsele drhqadiasy
361 qeaiqqldae lrntkwemaa qlreyqdlln vkmaldieia ayrkllegee crigfgpipf
421 slpeglpkip svsthikvks eekikvveks eketviveeq teetqvteev teeeekeake
481 eegkeeegge eeaeggeee tksppaeeaa spekeakspv keeakspaea kspekeeaks
541 paevkspeka kspakeeaks ppeakspeke akspaevks pekakspake akspaeaks
601 pekakspvke eakspaeaks pvkeeakspa evkspekaks ptkeeakspe kakspekaks
661 pekeeakspe kakspvkaea kspekakspv kaeakspeka kspvkeeaks pekakspvke
721 eakspekaks pvkeeaktpe kakspvkeea kspekakspe kaktldvksp eaktpakeea
781 rspadkfpek akspvkeevk spekakspl kedakapeke ipkkeevksp vkeeekpqev
841 kvkeppkkae eekapatpk teekkdskke eapkkeapkp kveekkepav ekpkeskvea
901 kkeeaedkkk vptpekeap akvevkedak pkektevakk epddakakep skpaekkeaa
961 pekkdtkeek akkpeekpkt eakakeddkt lskepskpka ekaeksssdt qkdskppeka
...

(human neurofilament medium chain amino acid sequence):
SEQ ID NO: 4

MSYTLDSLGNPSAYRRVTETRSSFSRVSGSPSSGFRSQSWSRGSPSTVSSSYKRSMLAPR

LAYSSAMLSSAESSLDFSQSSSLLNGGSGPGGDYKLSRSNEKEQLQGLNDRFAGYIEKVH

YLEQQNKEIEAEIQALRQKQASHAQLGDAYDQEIRELRATLEMVNHEKAQVQLDSDHLEE

-continued

DIHRLKERFEEEARLRDDTEAAIRALRKDIEEASLVKVELDKKVQSLQDEVAFLRSNHEE

EVADLLAQIQASHITVERKDYLKTDISTALKEIRSQLESHSDQNMHQAEEWFKCRYAKLT

EAAEQNKEAIRSAKEEIAEYRRQLQSKSIELESVRGTKESLERQLSDIEERHNHDLSSYQ

DTIQQLENELRGTKWEMARHLREYQDLLNVKMALDIEIAAYRKLLEGEETRFSTFAGSIT

GPLYTHRPPITISSKIQKPKVEAPKLKVQHKFVEEIIEETKVEDEKSEMEEALTAITEEL

AVSMKEEKKEAAEEKEEEPEAEEEEVAAKKSPVKATAPEVKEEEGEKEEEEGQEEEEEED

EGAKSDQAEEGGSEKEGSSEKEEGEQEEGETEAEAEGEEAEAKEEKKVEEKSEEVATKEE

LVADAKVEKPEKAKSPVPKSPVEEKGKSPVPKSPVEEKGKSPVPKSPVEEKGKSPVPKSP

VEEKGKSPVSKSPVEEKAKSPVPKSPVEEAKSKAEVGKGEQKEEEEKEVKEAPKEEKVEK

KEEKPKDVPEKKKAESPVKEEAVAEVVTITKSVKVHLEKETKEEGKPLQQEKEKEKAGGE

GGSEEEGSDKGAKGSRKEDIAVNGEVEGKEEVEQETKEKGSGREEEKGVVTNGLDLSPAD

EKKGGDKSEEKVVVTKTVEKITSEGGDGATKYITKSVTVTQKVEEHEETFEEKLVSTKKV

EKVTSHAIVKEVTQSD

SEQ ID NO: 5
MARHLREYQDLLNVKMALDIEIAAYRKLLEGEETRFSTFAGSITGPLYTHRPPITISSKIQKPKVEAPKL

KVQHKFVEEIIEETKVEDEKSEMEEALTAITEELAVSMKEEKKEAAEEKEEEPEAEEEEVAAKKSPVKA

T

APEVKEEEGEKEEEEGQEEEEEEDEGAKSDQAEEGGSEKEGSSEKEEGEQEEGETEAEAEGEEAEAKEE

K

KVEEKSEEVATKEELVADAKVEKPEKAKSPVPKSPVEEKGKSPVPKSPVEEKGKSPVPKSPVEEKGKSP

V

PKSPVEEKGKSPVSKSPVEEKAKSPVPKSPVEEAKSKAEVGKGEQKEEEEKEVKEAPKEEKVEKKEEKP

K

DVPEKKKAESPVKEEAVAEVVTITKSVKVHLEKETKEEGKPLQQEKEKEKAGGEGGSEEEGSDKGAK

GSR

KEDIAVNGEVEGKEEVEQETKEKGSGREEEKGVVTNGLDLSPADEKKGGDKSEEKVVVTKTVEKITSE

GG

DGATKYITKSVTVTQKVEEHEETFEEKLVSTKKVEKVTSHAIVKEVTQSD

SEQ ID NO: 6
MSFGSEHYLCSSSSYRKVFGDGSRLSARLSGAGGAGGFRSQSLSRSNVASSAACSSASSL

GLGLAYRRPPASDGLDLSQAAARTNEYKIIRTNEKEQLQGLNDRFAVFIEKVHQLETQNR

ALEAELAALRQRHAEPSRVGELFQRELRDLRAQLEEASSARSQALLERDGLAEEVQRLRA

RCEEESRGREGAERALKAQQRDVDGATLARLDLEKKVESLLDELAFVRQVHDEEVAELLA

TLQASSQAAAEVDVTVAKPDLTSALREIRAQYESLAAKNLQSAEEWYKSKFANLNEQAAR

STEAIRASREEIHEYRRQLQARTIEIEGLRGANESLERQILELEERHSAEVAGYQDSIGQ

LENDLRNTKSEMARHLREYQDLLNVKMALDIEIAAYRKLLEGEETRFSTSGLSISGLNPL

PNPSYLLPPRILSATTSKVSSTGLSLKKEEEEEEASKVASKKTSQIGESFEEILEETVIS

TKKTEKSNIEETTISSQKI

SEQ ID NO: 7
MSHHPSGLRAGFSSTSYRRTFGPPPSLSPGAFSYSSSSRFSSSRLLGSASPSSSVRLGSF

RSPRAGAGALLRLPSERLDFSMAEALNQEFLATRSNEKQELQELNDRFANFIEKVRFLEQ

QNAALRGELSQARGQEPARADQLCQQELRELRRELELLGRERDRVQVERDGLAEDLAALK

-continued

QRLEEETRKREDAEHNLVLFRKDVDDATLSRLELERKIESLMDEIEFLKKLHEEELRDLQ

VSVESQQVQQVEVEATVKPELTAALRDIRAQYESIAAKNLQEAEEWYKSKYADLSDAANR

NHEALRQAKQEMNESRRQIQSLTCEVDGLRGTNEALLRQLRELEEQFALEAGGYQAGAAR

LEEELRQLKEEMARHLREYQELLNVKMALDIEIATYRKLLEGEESRISVPVHSFASLNIK

TTVPEVEPPQDSHSRKTVLIKTIETRNGEVVTESQKEQRSELDKSSAHSY

CAGGATACATTTCTACAGCT    SEQ ID NO: 8

TTAATGTTTATCAGGAT   SEQ ID NO: 9

AGTGTTTAATGTTTATC   SEQ ID NO: 10

CCGTCGCCCTTCAGCACGCA    SEQ ID NO: 11

CCTTCCCTGAAGGTTCCTCC    SEQ ID NO: 12

CCTATAGGACTATCCAGGAA    SEQ ID NO: 13

The following examples are provided which are meant to illustrate but not limit the invention described herein.

Example 1: A Therapeutic that is not Efficacious for ALS

A clinical trial was performed to look at whether a candidate therapeutic, dexpramipexole, had an ability to alleviate ALS symptoms.

The results showed that administration of depramipexole did not reduce ALS symptoms.

A retrospective look at the level of a neurofilament protein, namely neurofilament heavy chain, in the serum of the patients treated with dexpramipexole. Determination of baseline as well as longitudinal plasma neurofilament heavy chain (NFH) concentrations in the clinical trial of dexpramipexole, EMPOWER, and assessment of their relationship to clinical outcomes including survival and the rates of decline of muscle strength (assessed by hand-held dynamometry [HHD]), slow vital capacity (SVC), and ALSFRS-R).

Neurofilaments, comprising heteropolymers of light, intermediate, and heavy chains, are major structural components of mature axons. Patients with neurodegenerative diseases manifest elevated CSF and plasma levels of neurofilaments, presumably representing extracellular release of the axonal contents of degenerating neurons. In observational and largely cross-sectional data from ALS patients, correlations have been demonstrated between NF levels and disease severity, as indicated by rates of survival and ALSFRS-R decline EMPOWER was a Phase 3 global randomized clinical trial (RCT) of the safety and efficacy of dexpramipexole in the treatment of ALS conducted at 81 academic medical centers enrolling 943 adults (see Cudkowicz M E et al., Lancet Neurol. 2013 November; 12(11):1059-67).

The subjects included in the EMPOWER study had to have a diagnosis of possible, probable, or definite ALS, have had ALS symptoms for fewer than 24 months, have an SVC value that was at least 65% of the predicted value, and no significant comorbidities.

In the study, the subjects were allocated in a 1:1 ratio to treatment with dexpramipexole or placebo for 12 months, Plasma neurofilament heavy (NFH), measured using a NFH assay on the Ella, an automated microfluidic cartridge based immunoassay platform from Protein Simple.

The results are shown in Table 1.

TABLE 1

Plasma NFH was measured in a large and representative subset of EMPOWER.

| Variable | NFH not measured | NFH measured | Overall |
|---|---|---|---|
| Number | 279 (30%) | 663 (70%) | 942 (100%) |
| Baseline | | | |
| Age | 57.7 (11.6) | 56.8 (11.2) | 57.1 (11.3) |
| Sex: Female | 35.8% | 35.7% | 35.8% |
| Symptoms duration | 15.3 (5.4) | 15.2 (5.3) | 15.2 (5.3) |
| Baseline ALSFRS-R | 38.4 (5.0) | 38.1 (5.6) | 38.2 (5.4) |
| Riluzole use | 73.1% | 76.0% | 75.2% |
| Onset: Bulbar | 23.3% | 23.3% | 23.3% |
| On Study | | | |
| Number on treatment | 51.6% | 49.8% | 50.3% |
| Slope of ALSFRS | −1.2 (1.1) | −1.2 (0.9) | −1.2 (1.0) |
| Death | 17.6% | 15.7%) | 16.2% |

Figure 2:
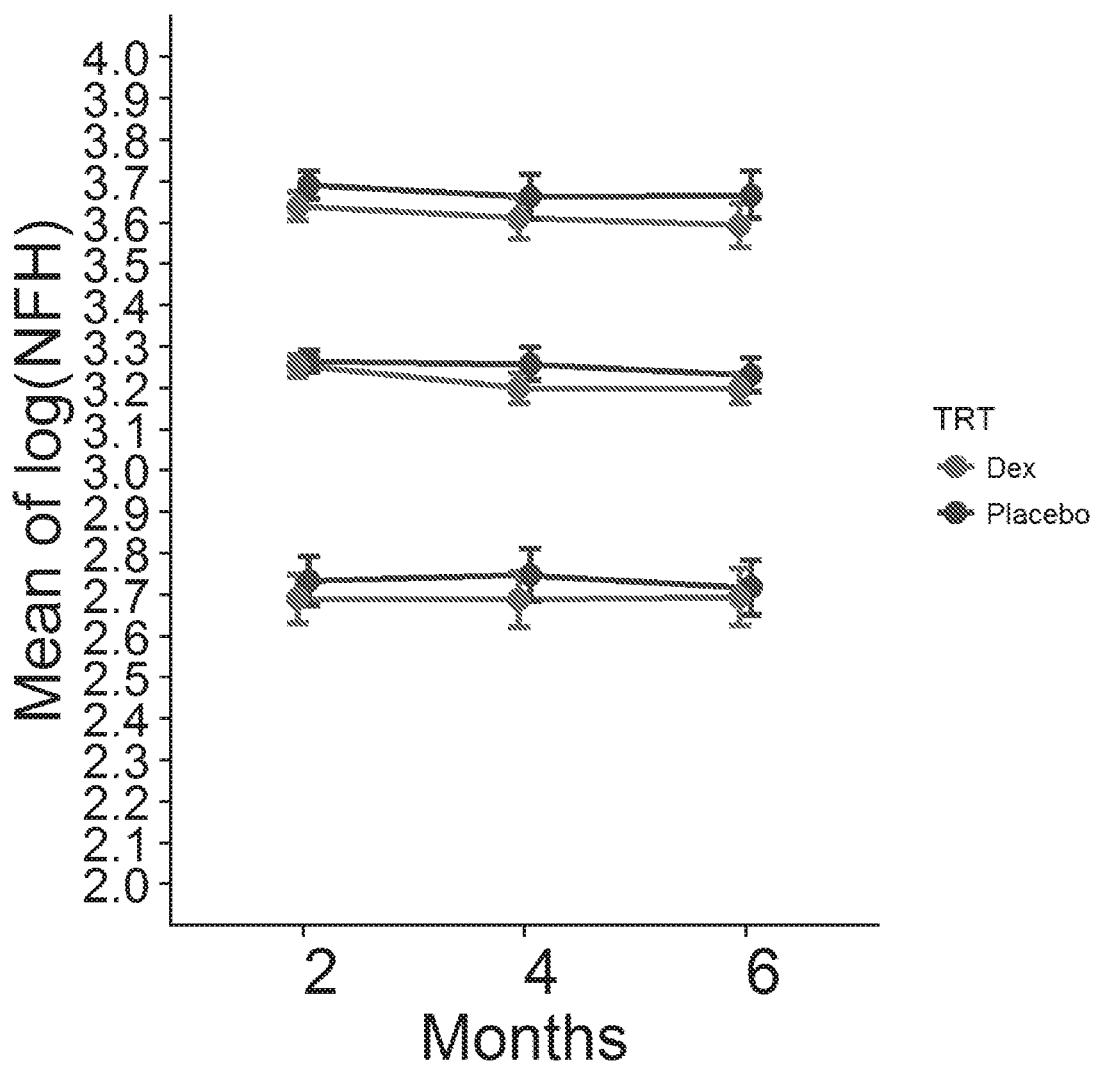
FIG. 2 is a line graph showing the longitudinal change in plasma neurofilament heavy chain levels by treatment group in patients in the upper tertile, middle tertile, and lower tertile of neurofilament heavy chain levels. For each tertile, the placebo-treated group is the upper line and the dexpramipexole-treated group is the lower line.

After adjusting for multiple covariates, baseline plasma NFH (log 10 transformed) was correlated as follows:

during-study survival (HR=2.41, p<0.001)

rate of decline in HHD (b=−0.026, p<0.001, adj. $r^2$=0.14), rate of decline in SVC (b=−1.77, p<0.001, adj. $r^2$=0.20), rate of decline in ALSFRS-R (b=−0.61, p<0.001, adj. $r^2$=0.20);

The mean plasma neurofilament heavy chain levels declined by 1.8% per month (see FIG. 1). However, the findings showed that there was no difference in longitudinal plasma NFH course between subjects assigned to placebo vs. dexpramiexole, a therapy that was without clinical efficacy in this EMPOWER study (see FIG. 2).

Example 2: Administration of a Therapeutic Expected to be Efficacious in ALS Patients Resulted in a Decline in Serum Neurofilament Levels Mutations in superoxide dismutase 1 (SOD1) are responsible for 20% of familial ALS. Given the gain of toxic function in this dominantly inherited disease, lowering SOD1 mRNA and protein may provide therapeutic benefit.

An antisense oligonucleotide (ASO) targeting SOD1 has been that reduces SOD1 mRNA and protein and extend survival by more than 50 days in SOD1$^{G93A}$ rats and by almost 40 days in SOD1$^{G93A}$ mice.

As shown below, the initial loss of compound muscle action potential in SOD1$^{G93A}$ mice is reversed after a single dose of SOD1 ASO. Furthermore, increases in serum phospho-neurofilament heavy chain levels are stopped by SOD1 ASO therapy.

The antisense oligonucleotides used were as follows in Table 2.

TABLE 2

| ASO Name | Sequence/Chemistry |
|---|---|
| ASO1 | CAoGGoATACATTTCTACoAGoCT (SEQ ID NO: 8) |
| ASO2 | TToAoATGTTTATCAoGoGAT (SEQ ID NO: 9) |
| ASO3 | AGoToGTTTAATGTToToATC (SEQ ID NO: 10) |
| 333611 | CCGTCGCCCTTCAGCACGCA (SEQ ID NO: 11) |
| Inactive ASO (in vitro) | CCTTCCCTGAAGGTTCCTCC (SEQ ID NO: 12) |
| Inactive ASO (in vivo) | CCoToAoTAGGACTATCCAoGoGoAA (SEQ ID NO: 13) |

The 6 antisense oligonucleotides shown in Table 2 contain phosphorothioate backbone modifications (with "o" indicating unmodified phosphodiester linkages), 2'-O-methoxyethylribose (MOE; bold), and (S)-2',4'-constrained 2'-O-ethyl (cEt; italics) groups in the 5' and 3' wings. The ASOs were targeted to the 3' UTR of SOD1 mRNA (ASO1, AS02, and AS03), exon 1 of SOD1 mRNA (333611), or nothing in the rodent genome (inactive ASOs). The sequences evaluated and the location of chemical modifications are provided. Different control (inactive) ASOs were used for in vitro and in vivo studies. All cytosine residues are 5' methylcytosine.

In a human neuroblastoma cell line (SH-SY5Y), these ASOs (ASO1 and AS02) potently lowered SOD1 mRNA in a dose-dependent manner.

Treatment with SOD1-lowering ASO significantly delayed disease onset and extends survival in SOD1$^{G93A}$ mice and rats. Expression of mutant SOD1 in SOD1$^{G93A}$ rodent models is known to cause severe atrophy of the limbs and trunk that leads to loss of motor function and eventually death).

To investigate whether a SOD1-lowering ASO strategy could delay disease parameters, SOD1$^{G93A}$ mice (B6.CgTg (SOD1*G93A)Gur/J) were infused Intracerebroventricular (i.e.v.) with bolus doses of 300 μg ASO1 at 50 and 94 days of age. Weight and performance on rotarod were tested weekly. Mice that received ASO1 maintained weight 26 days longer and performed better on rotarod than mice injected with a control inactive ASO (inactive ASO) at similar concentrations (data not shown). Median survival for ASO1-treated mice was 37 days longer compared with inactive ASO, representing a 22% extension of survival in the mouse model SOD1$^{G93A}$ rats (Taconic Biosciences, model 2148) received a 30-μl intrathecal bolus injection via polyethylene catheter placed between the L3 and L5 vertebrae of the lumber spinal cord. 65-day-old rats were given 1000 μg ASO1, AS02, AS03, ASO 333611, inactive ASO, or an artificial cerebrospinal fluid (aCSF) vehicle control. All ASOs were diluted in aCSF. All treatment groups were sexual phenotype- and litter-matched to control for drift in copy count or sexual phenotype-induced variances.

The results showed that rats treated with ASO1 or AS02 maintained weight 70 days (P<0.0001) and 67 days (P<0.001) longer, respectively, than rats treated with aCSF. 333611 delayed onset of weight loss modestly (median 139 days, compared with aCSF median 121 days).

There was no significant difference in the onset or survival between the 80-day active ASO treatment and the 110-day active ASO treatment.

Figure 3:
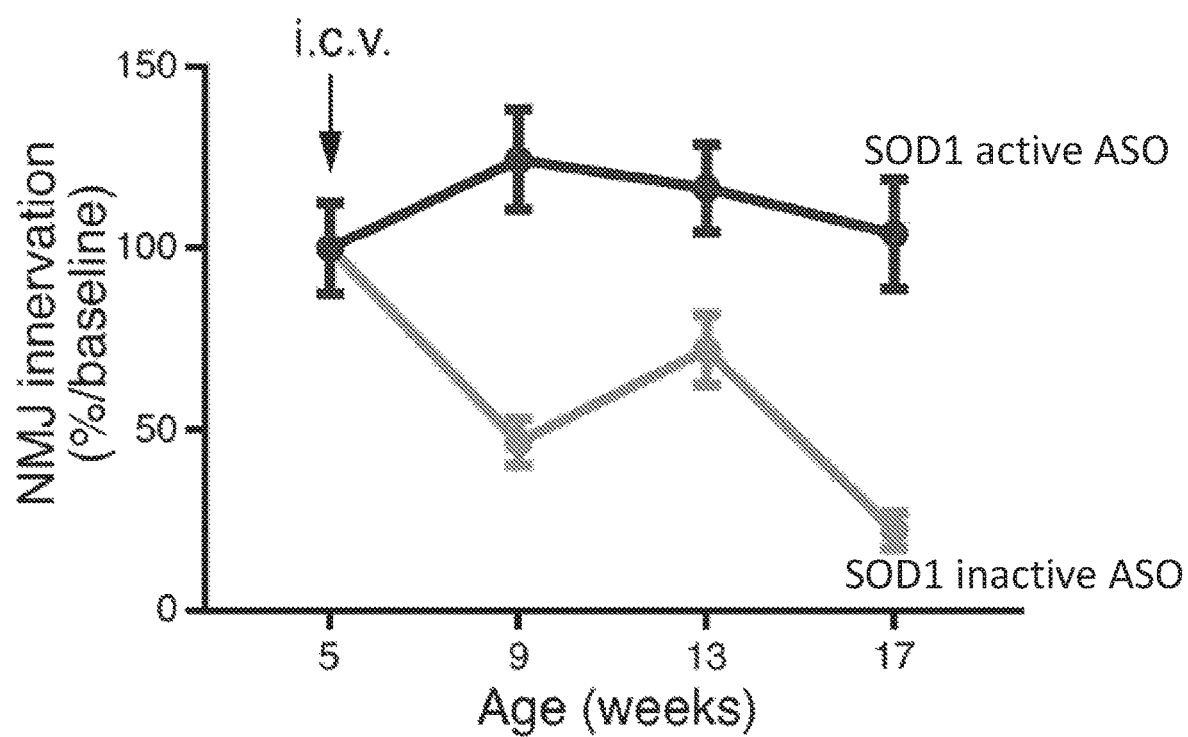
FIG. 3 is a line graph comparing neuromuscular junction loss (NMJ) in SOD1$^{G93A}$ mice treated with SOD1 active ASO or SOD1 inactive ASO.
Figure 4:
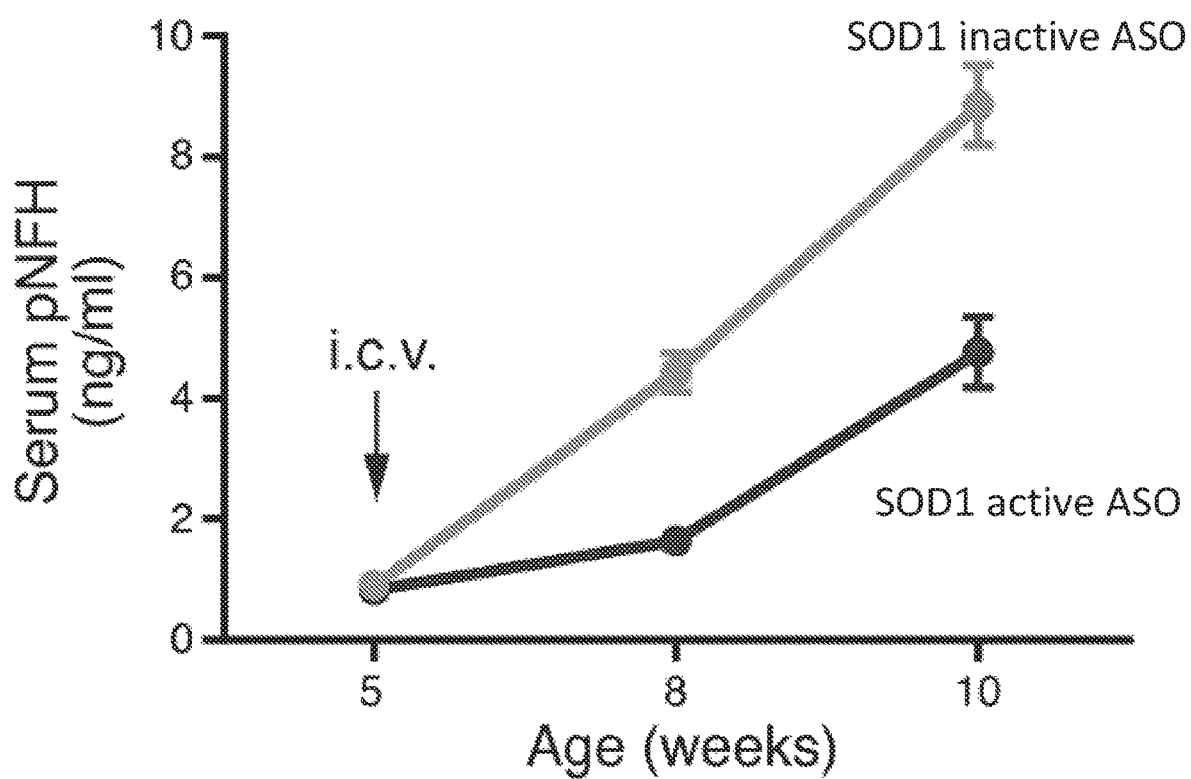
FIG. 4 is a line graph comparing phosphorylated neurofilament heavy chain levels in serum of SOD1$^{G93A}$ mice treated with SOD1 active ASO or SOD1 inactive ASO.

To test whether SOD1 reduction by ASO could affect markers of disease, SOD1$^{G93A}$ mice were injected intraventricularly once at 5 weeks of age with 100 μg ASO1 and evaluated for changes in compound muscle action potential (CMAP), neuromuscular junction innervation, and serum phospho-neurofilament heavy chain (pNfH) levels. In SOD1$^{G93A}$ mice, CMAP declines over time, preceding the loss of motor neurons. SOD1$^{G93A}$ mice treated with ASO1 at 5 weeks maintained CMAP over the next 12 weeks, whereas the control-treated animals' CMAP was reduced by more than half over the same time period (data not shown). Consistent with CMAP electrophysiological demonstration of preserved muscle function, ASO1-treated mice (injected once at 5 weeks of age with a single dose of 300 μg ASO1) maintained innervation of the tibialis anterior muscles in the hind limbs, whereas control-treated animals showed evidence of denervation of more than 75% of muscle endplates (FIG. 3, n=12 per group; average±SEM).

pNfH increases in CSF and serum in ALS rodent models, human patients with ALS, and other neurodegenerative diseases. To look at phosphorylated neurofilament heavy chain levels in the serum, blood was collected at baseline (5 weeks) before i.e.v. injection, and then again at 8 and 10 weeks of age from the SOD1$^{G93A}$ mutant mice injected once at 5 weeks of age with a single dose of 300 μg ASO1). pNfH serum levels were measured through the ELLA microfluidic ELISA platform (Protein Simple) according to the manufacturer's instructions. Briefly, a maximum of 100 μl blood was collected through facial vein puncture at the indicated time points. Serum samples were prepared by centrifugation of BD Vacutainer SST tubes (BD Diagnostics) and stored at −80° C. until used. As shown in FIG. 4, SOD1 mice treated with active ASO1 showed lower levels of pNfH compared with SOD1 mice treated with control ASO (i.e., SOD1 inactive ASO) ((n=12 per group; average±SEM in FIG. 4)).

Based on the results from this Example 2 in the rat and murine models, and the fact that the SOD1 active ASO is able to reduce serum levels of phosphorylated neurofilament level heavy chain, it is expected that the SOD1 active ASO will be an efficacious therapeutic for alleviating the symptoms of ALS in ALS patients.

Example 3: Switching Therapeutics in an ALS Patient

In this prophetic example, a patient recently diagnosed with ALS and having an ALSFRS-R score of 31 is treated with riluzole. The patient's serum neurofilament protein level is measured and is determined to be at a level which will be called the initial level. The patient's physician will ask the patient to take an ALSFRS-R assessment every six months. But after 3 months (i.e., prior to taking the ALSFRS-R test), the physician measures the patient's serum neurofilament protein level and discovers that the patient's serum neurofilament protein level is higher than the initial level. The physician will then advise the patient to switch to another therapeutic (e.g., edarovone that may be efficacious to that patient) prior to the patient taking his six month ALSFRS-R test. It is predicted that if the patient switch therapeutics, his next ALSFRS-R test (i.e., 3 months after switching) will be higher than if the patient had remained on riluzole if the new therapeutic (e.g., edarovone) is efficacious to the patient.

Example 4: Administration of an ALS Therapeutic Resulted in a Decline in Neurofilament Levels A double-blind, randomized, placebo-controlled, clinical trial was conducted in SOD1 ALS patients. The trial involved single and multiple ascending dose (SAD/MAD) studies. In the MAD portion, participants received 5 doses of study drug over approximately 3 months. Fifty adult participants with SOD1 mutation were randomized 3:1 (ASO: placebo) per cohort to receive 20 mg, 40 mg, 60 mg, or 100 mg of placebo or a SOD-1 decreasing ASO-ASO1 (SEQ ID NO:8). Between 1 and 4 ASO1-treated participants per cohort had a documented SOD1 mutation that was adjudicated a priori to be fast-progressing (primarily A4V).

Reductions in SOD1 Levels

Figure 5:
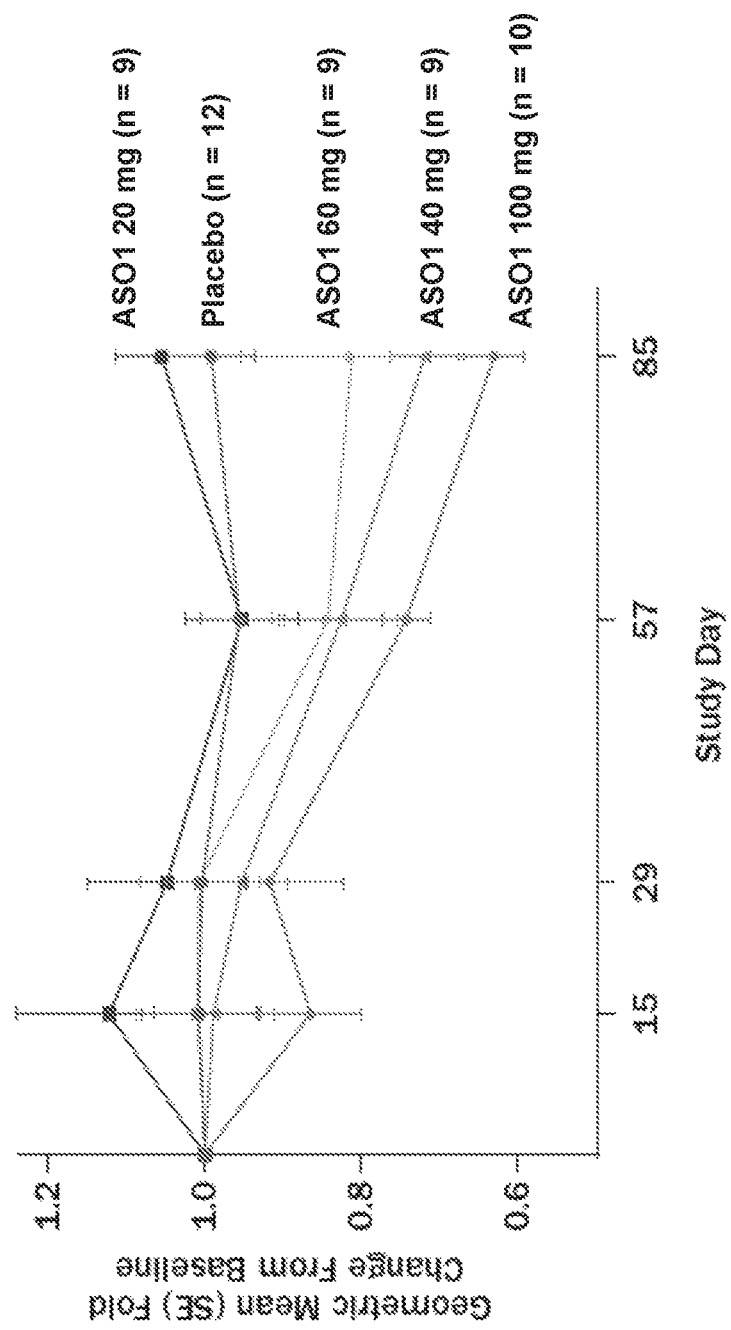
FIG. 5 is a graph showing the fold change from baseline of CSF SOD1 protein concentrations in various ASO1 dosing cohorts.

Reductions from baseline in CSF SOD1 concentrations were observed in the 40 mg, 60 mg, and 100 mg cohorts, which increased with dosage amount and over time had maximal reductions in the 100 mg-treated group at Day 85. See FIG. 5. Modeling based on preclinical data suggest that ASO1 at 100 mg effectively reduces SOD1 levels in the spinal cord by >99% and approximately by 25-30% in the cortex.

Clinical Observations

Figure 6A:
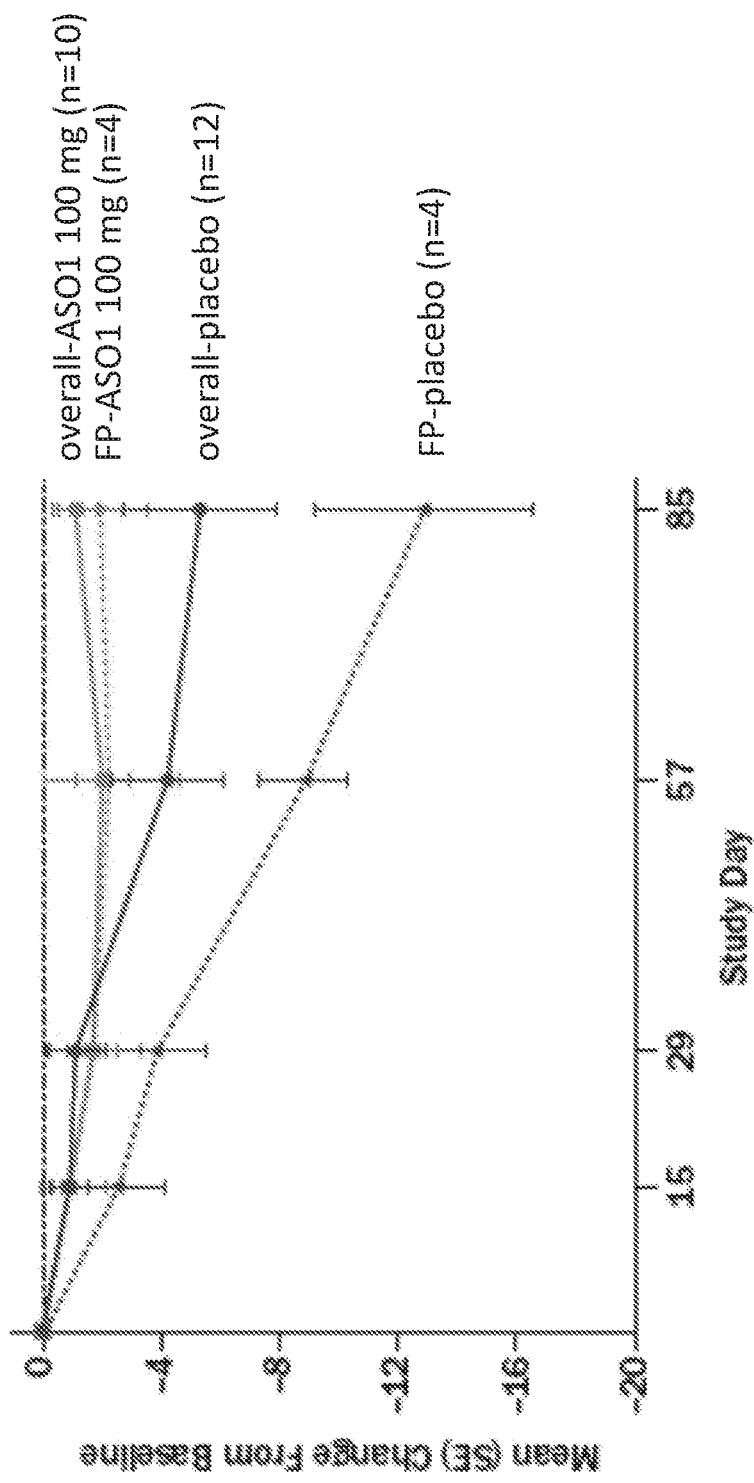
FIG. 6A is a graph showing the mean change from baseline in ALSFRS-R in patients who were fast progressors treated with ASO1 100 mg versus placebo and in patients with overall SOD1 mutations (fast progressing and other SOD1 mutations) treated with ASO1 100 mg versus placebo.
Figure 6B:
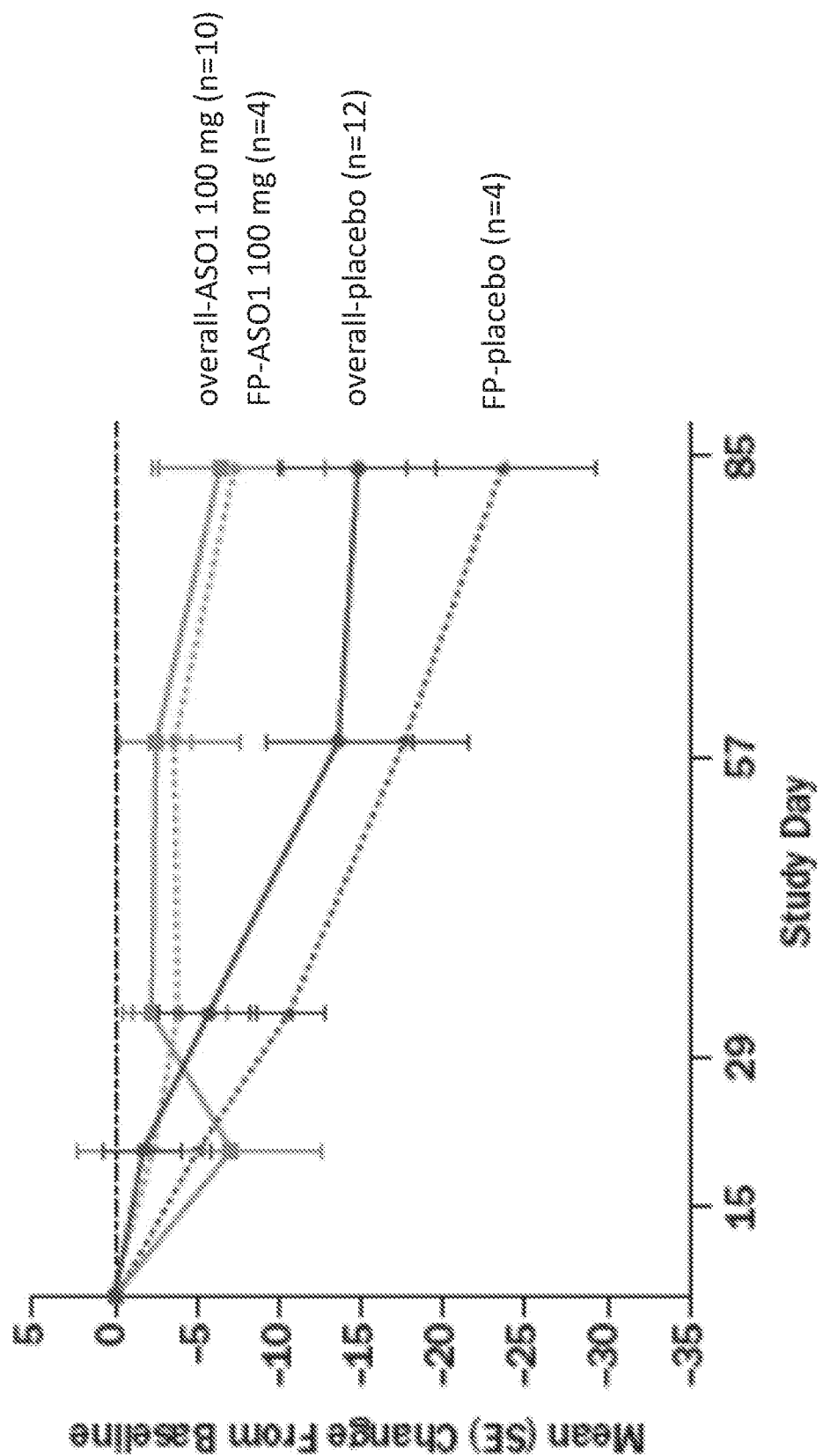
FIG. 6B is a graph showing the mean change from baseline in SVC (% predicted) in patients who were fast progressors treated with ASO1 100 mg versus placebo and in patients with overall SOD1 mutations (fast progressing and other SOD1 mutations) treated with ASO1 100 mg versus placebo.
Figure 7A:
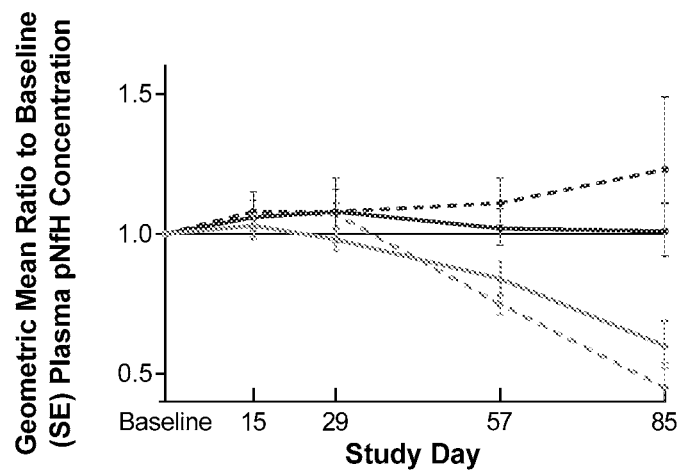
FIG. 7A is a graph showing pNfH levels in plasma during the course of treatment with ASO1 100 mg or placebo.
Figure 7B:
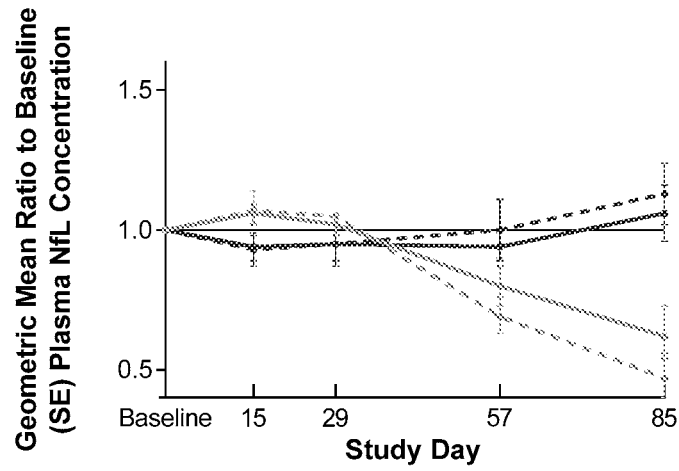
FIG. 7B is a graph showing NfL levels in plasma during the course of treatment with ASO1 100 mg or placebo.
Figure 7C:
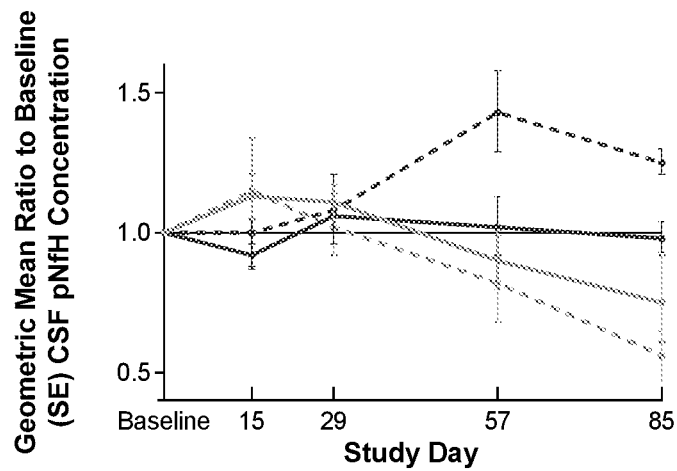
FIG. 7C is a graph showing pNfH levels in CSF during the course of treatment with ASO1 100 mg or placebo.
Figure 7D:
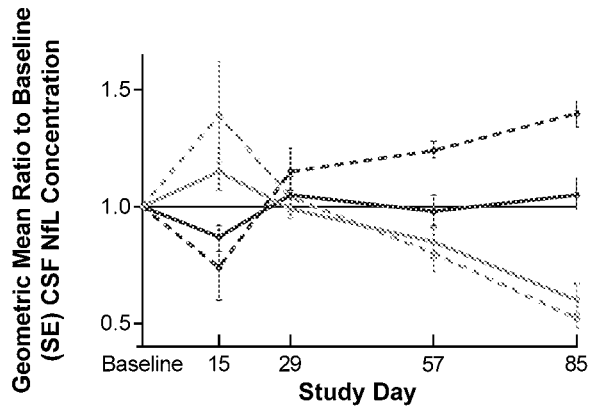
FIG. 7D is a graph showing NfL levels in CSF during the course of treatment with ASO1 100 mg or placebo.

Treatment with ASO1 demonstrated a slowing of functional decline (ALSFRS-R) and a slowing of decline in respiratory function (as measured by SVC) compared to placebo. See FIGS. 6A and 6B. In participants with fast-progressing SOD1 mutations, a greater difference between the ASO1 100 mg and placebo groups was observed across these measures compared with those with other mutations.

CSF Phosphorylated Neurofilament Heavy Chain (pNfH) Levels

Lowering of CSF pNfH was observed in the ASO1 100 mg cohort compared with placebo, and a greater difference between the ASO1 100 mg and placebo groups was observed in participants with fast-progressing SOD1 mutations. In patients with fast-progressing SOD1 mutations, treatment with ASO1 resulted in a reduction in CSF pNfH levels and a slowing of clinical decline compared to placebo. FIG. 6C shows a difference in pNfH levels at day 85 between the ASO1 100 mg and placebo groups observed in patients with fast-progressing SOD1 mutations.

Plasma and CSF pNfH and Neurofilament Light Chain (NfL) Levels

Baseline pNfH and NfL levels were highest in fast progressing patients and correlated with disease activity (as measured by ALSFRS-R prerandomization slope). A reduction in both pNfH and NfL levels was observed with ASO1 100 mg treatment over time, in both plasma and CSF, as compared with an apparent stabilization or increase with placebo. See FIGS. 7A-7D. In FIGS. 7A-7D, overall placebo (n=12) is the solid line at, near, or above the 1.0 baseline measure throughout the study; overall ASO1 100 mg treatment (n=10) is the solid line declining below the 1.0 baseline measure throughout the study; fast progressing placebo (n=4) is the dotted line at, near, or above the 1.0 baseline measure throughout the study; and fast progressing ASO1 100 mg treatment (n=4) is the dotted line declining below the 1.0 baseline measure throughout the study. pNfH levels were assessed using the ProteinSimple™ Simple Plex Ella immunoassay. NfL levels were assessed using the Quanterix Simoa NfL Advantage assay.

Thus, without wishing to be bound by any particular theory, the results provided herewith support the use of neurofilament protein levels (e.g., serum and/or CSF neurofilament protein levels) as a marker (e.g., a pharmacodynamic marker) to determine if a therapeutic that an ALS patient is being treated with is actually efficacious for that patient. For example, if a patient is previously on a non-efficacious therapeutic and still has increasing ALS symptoms, measuring the serum neurofilament levels may give advance notice, before irreversible functional decline occurs, that the therapeutic is not efficacious and should be switched to a new therapeutic that may be efficacious to that patient.

The embodiments of the invention described above are intended to be merely exemplary; numerous variations and modifications will be apparent to those skilled in the art. All such variations and modifications are intended to be within the scope of the present invention as defined in any appended claims.

The invention claimed is:

1. A method comprising:
   (a) administering a dose comprising an antisense compound to a patient with amyotrophic lateral sclerosis (ALS), wherein the antisense compound has the following formula:

mCes Aeo Ges Geo Aes Tds Ads mCds Ads Tds Tds Tds mCds Tds Ads mCeo Aes Geo mCes Te (nucleobase sequence of SEQ ID NO:8),
   wherein, A=an adenine,
   mC=a 5-methylcytosine,
   G=a guanine,
   T=a thymine,
   e=a 2'-O-methoxyethylribose modified sugar,
   d=a 2'-deoxyribose sugar,
   s=a phosphorothioate internucleoside linkage, and
   o=a phosphodiester internucleoside linkage; and
   (b) determining a level of a neurofilament protein in a biological sample from the patient,
   wherein the level of the neurofilament protein in the biological sample of the patient is lower than a level of neurofilament protein in a patient with ALS not administered the antisense compound, and
   wherein the neurofilament protein is a phosphorylated neurofilament heavy chain or a neurofilament light chain.

2. The method of claim 1, further comprising administering additional doses of the antisense compound to the patient after measuring a neurofilament protein level in the biological sample of the patient that is lower than the neurofilament protein level in the patient with ALS not administered the antisense compound.

3. The method of claim 1, wherein the patient has a mutation in the superoxide dismutase 1 (SOD1) gene associated with amyotrophic lateral sclerosis.

4. The method of claim 3, wherein the mutation in the SOD1 gene is A4V.

5. The method of claim 3, wherein the mutation in the SOD1 gene is A4V, H46R, G93S, A4T, G141X, D133A, V148G, N139K, G85R, G93A, V14G, C6S, I113T, G37R, A89V, E100G, D90A, T137A, E100K, G41A, G41D, G41S, G13R, G72S, L8V, F20C, Q22L, H48R, T54R, 5591, V87A, T88deltaTAD, A89T, V97M, S105deltaSL, V118L, D124G, L114F, D90A, G12R, or G147R.

6. The method of claim 1, wherein the biological sample comprises blood, serum, plasma, or cerebral spinal fluid.

7. A method comprising:
(a) measuring a neurofilament protein level in a first biological sample obtained from a human subject;
(b) administering one or more doses of an antisense compound to the human subject, wherein the antisense compound has the following formula:

mCes Aeo Ges Geo Aes Tds Ads mCds Ads Tds Tds Tds mCds Tds Ads mCeo Aes Geo mCes Te (nucleobase sequence of SEQ ID NO: 8), wherein, A=an adenine,
mC=a 5-methylcytosine,
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage;
or a pharmaceutically acceptable salt thereof; and
(c) measuring a neurofilament protein level in a second biological sample obtained from the human subject after administering the one or more doses of the antisense compound,
wherein the neurofilament protein level in the second biological sample is lower than the neurofilament protein level in the first biological sample, and
wherein the neurofilament protein is a phosphorylated neurofilament heavy chain or a neurofilament light chain.

8. The method of claim 7, further comprising administering additional doses of the antisense compound to the human subject after measuring a neurofilament protein level in the second biological sample that is lower than the neurofilament protein level in the first biological sample.

9. The method of claim 7, wherein the patient-er the human subject has a mutation in the superoxide dismutase 1 (SOD1) gene associated with amyotrophic lateral sclerosis.

10. The method of claim 9, wherein the mutation in the SOD1 gene is A4V.

11. The method of claim 9, wherein the mutation in the SOD1 gene is A4V, H46R, G93S, A4T, G141X, D133A, V148G, N139K, G85R, G93A, V14G, C6S, I113T, G37R, A89V, E100G, D90A, T137A, E100K, G41A, G41D, G41S, G13R, G72S, L8V, F20C, Q22L, H48R, T54R, S591, V87A, T88deltaTAD, A89T, V97M, S105deltaSL, V118L, D124G, L1 14F, D90A, G12R, or G147R.

12. The method of claim 7, wherein the first biological sample and the second biological sample comprise blood, serum, plasma, or cerebral spinal fluid.

* * * * *

SEQUENCE LISTING

<160> NUMBER OF SEQ ID NOS: 13

<210> SEQ ID NO 1
<211> LENGTH: 543
<212> TYPE: PRT
<213> ORGANISM: Homo sapiens

<400> SEQUENCE: 1

Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

-continued

```
Tyr Ser Thr Ala Arg Ser Ala Tyr Ser Ser Tyr Ser Ala Pro Val Ser
         35                  40                  45

Ser Ser Leu Ser Val Arg Arg Ser Tyr Ser Ser Ser Gly Ser Leu
 50                  55                  60

Met Pro Ser Leu Glu Asn Leu Asp Leu Ser Gln Val Ala Ala Ile Ser
 65                  70                  75                  80

Asn Asp Leu Lys Ser Ile Arg Thr Gln Glu Lys Ala Gln Leu Gln Asp
                 85                  90                  95

Leu Asn Asp Arg Phe Ala Ser Phe Ile Glu Arg Val His Glu Leu Glu
                100                 105                 110

Gln Gln Asn Lys Val Leu Glu Ala Glu Leu Leu Val Leu Arg Gln Lys
            115                 120                 125

His Ser Glu Pro Ser Arg Phe Arg Ala Leu Tyr Glu Gln Glu Ile Arg
130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
                180                 185                 190

Met Glu Ala Arg Lys Gly Ala Asp Glu Ala Ala Leu Ala Arg Ala Glu
            195                 200                 205

Leu Glu Lys Arg Ile Asp Ser Leu Met Asp Glu Ile Ser Phe Leu Lys
210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
            260                 265                 270

Met Gln Asn Ala Glu Glu Trp Phe Lys Ser Arg Phe Thr Val Leu Thr
275                 280                 285

Glu Ser Ala Ala Lys Asn Thr Asp Ala Val Arg Ala Ala Lys Asp Glu
290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335

Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
                355                 360                 365

Leu Lys Glu Tyr Gln Asp Leu Leu Asn Val Lys Met Ala Leu Asp Ile
            370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
                405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
435                 440                 445

Glu Glu Gln Ile Glu Val Glu Glu Thr Ile Glu Ala Ala Lys Ala Glu
```

-continued

```
            450                 455                 460
Glu Ala Lys Asp Glu Pro Ser Glu Gly Glu Ala Glu Glu Glu
465                 470                 475                 480

Lys Asp Lys Glu Glu Ala Glu Glu Glu Ala Ala Glu Glu Glu
                485                 490                 495

Ala Ala Lys Glu Glu Ser Glu Glu Ala Lys Glu Glu Glu Gly Gly
                500                 505                 510

Glu Gly Glu Gly Glu Glu Thr Lys Glu Ala Glu Glu Glu Lys
                515                 520                 525

Lys Val Glu Gly Ala Gly Glu Glu Gln Ala Ala Lys Lys Lys Asp
530                 535                 540

<210> SEQ ID NO 2
<211> LENGTH: 1026
<212> TYPE: PRT
<213> ORGANISM: Homo sapiens

<400> SEQUENCE: 2

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
                20                  25                  30

Gly Ala Gly Gly Thr Arg Ser Ala Ala Gly Ser Ser Ser Gly Phe His
            35                  40                  45

Ser Trp Thr Arg Thr Ser Val Ser Val Ser Ala Ser Pro Ser Arg
50                  55                  60

Phe Arg Gly Ala Gly Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
        115                 120                 125

Ala Ala Ala Leu Arg Gln Gln Ala Gly Arg Ser Ala Met Gly Glu
        130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Arg Ala Leu Ala Arg Phe Ala Gln Glu
        195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285
```

```
Ser Glu Glu Trp Phe Arg Val Arg Leu Asp Arg Leu Ser Glu Ala Ala
290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
            325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
            355                 360                 365

Ala Glu Leu Arg Asn Thr Lys Trp Glu Met Ala Ala Gln Leu Arg Glu
370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
            435                 440                 445

Lys Ser Glu Lys Glu Thr Val Ile Val Glu Glu Gln Thr Glu Glu Thr
450                 455                 460

Gln Val Thr Glu Glu Val Thr Glu Glu Glu Lys Glu Ala Lys Glu
465                 470                 475                 480

Glu Glu Gly Lys Glu Glu Gly Gly Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
            515                 520                 525

Glu Ala Lys Ser Pro Glu Lys Glu Glu Ala Lys Ser Pro Ala Glu Val
            530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
                565                 570                 575

Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
            595                 600                 605

Lys Glu Glu Ala Lys Ser Pro Ala Glu Ala Lys Ser Pro Val Lys Glu
            610                 615                 620

Glu Ala Lys Ser Pro Ala Glu Val Lys Ser Pro Glu Lys Ala Lys Ser
625                 630                 635                 640

Pro Thr Lys Glu Ala Lys Ser Pro Glu Lys Ala Lys Ser Pro Glu
                645                 650                 655

Lys Ala Lys Ser Pro Glu Lys Glu Ala Lys Ser Pro Glu Lys Ala
                660                 665                 670

Lys Ser Pro Val Lys Ala Glu Ala Lys Ser Pro Glu Lys Ala Lys Ser
            675                 680                 685

Pro Val Lys Ala Glu Ala Lys Ser Pro Glu Lys Ala Lys Ser Pro Val
            690                 695                 700

Lys Glu Glu Ala Lys Ser Pro Glu Lys Ala Lys Ser Pro Val Lys Glu
```

```
                705                 710                 715                 720
    Glu Ala Lys Ser Pro Glu Lys Ala Lys Ser Pro Val Lys Glu Glu Ala
                    725                 730                 735

Lys Thr Pro Glu Lys Ala Lys Ser Pro Val Lys Glu Glu Ala Lys Ser
                    740                 745                 750

Pro Glu Lys Ala Lys Ser Pro Glu Lys Ala Lys Thr Leu Asp Val Lys
                    755                 760                 765

Ser Pro Glu Ala Lys Thr Pro Ala Lys Glu Glu Ala Arg Ser Pro Ala
                    770                 775                 780

Asp Lys Phe Pro Glu Lys Ala Lys Ser Pro Val Lys Glu Glu Val Lys
    785                 790                 795                 800

Ser Pro Glu Lys Ala Lys Ser Pro Leu Lys Glu Asp Ala Lys Ala Pro
                    805                 810                 815

Glu Lys Glu Ile Pro Lys Lys Glu Val Lys Ser Pro Val Lys Glu
                    820                 825                 830

Glu Glu Lys Pro Gln Glu Val Lys Val Lys Glu Pro Pro Lys Lys Ala
                    835                 840                 845

Glu Glu Glu Lys Ala Pro Ala Thr Pro Lys Thr Glu Glu Lys Lys Asp
                    850                 855                 860

Ser Lys Lys Glu Glu Ala Pro Lys Lys Glu Ala Pro Lys Pro Lys Val
    865                 870                 875                 880

Glu Glu Lys Lys Glu Pro Ala Val Glu Lys Pro Lys Glu Ser Lys Val
                    885                 890                 895

Glu Ala Lys Lys Glu Ala Glu Asp Lys Lys Val Pro Thr Pro
                    900                 905                 910

Glu Lys Glu Ala Pro Ala Lys Val Glu Val Lys Glu Asp Ala Lys Pro
                    915                 920                 925

Lys Glu Lys Thr Glu Val Ala Lys Glu Pro Asp Asp Ala Lys Ala
                    930                 935                 940

Lys Glu Pro Ser Lys Pro Ala Glu Lys Lys Glu Ala Ala Pro Glu Lys
    945                 950                 955                 960

Lys Asp Thr Lys Glu Glu Lys Ala Lys Lys Pro Glu Glu Lys Pro Lys
                    965                 970                 975

Thr Glu Ala Lys Ala Lys Glu Asp Asp Lys Thr Leu Ser Lys Glu Pro
                    980                 985                 990

Ser Lys Pro Lys Ala Glu Lys Ala Glu Lys Ser Ser Ser Thr Asp Gln
                    995                 1000                1005

Lys Asp Ser Lys Pro Pro Glu Lys Ala Thr Glu Asp Lys Ala Ala
        1010                1015                1020

Lys Gly Lys
    1025

<210> SEQ ID NO 3
<211> LENGTH: 1020
<212> TYPE: PRT
<213> ORGANISM: Homo sapiens

<400> SEQUENCE: 3

Met Met Ser Phe Gly Gly Ala Asp Ala Leu Leu Gly Ala Pro Phe Ala
    1               5                   10                  15

Pro Leu His Gly Gly Ser Leu His Tyr Ala Leu Ala Arg Lys Gly
                    20                  25                  30

Gly Ala Gly Gly Thr Arg Ser Ala Ala Gly Ser Ser Ser Gly Phe His
                    35                  40                  45
```

```
Ser Trp Thr Arg Thr Ser Val Ser Ser Val Ser Ala Ser Pro Ser Arg
    50              55              60

Phe Arg Gly Ala Gly Ala Ala Ser Ser Thr Asp Ser Leu Asp Thr Leu
65              70              75                      80

Ser Asn Gly Pro Glu Gly Cys Met Val Ala Val Ala Thr Ser Arg Ser
                85              90                  95

Glu Lys Glu Gln Leu Gln Ala Leu Asn Asp Arg Phe Ala Gly Tyr Ile
            100             105             110

Asp Lys Val Arg Gln Leu Glu His Asn Arg Ser Leu Glu Gly Glu
            115             120             125

Ala Ala Ala Leu Arg Gln Gln Ala Gly Arg Ser Ala Met Gly Glu
    130             135             140

Leu Tyr Glu Arg Glu Val Arg Glu Met Arg Gly Ala Val Leu Arg Leu
145             150             155             160

Gly Ala Ala Arg Gly Gln Leu Arg Leu Glu Gln His Leu Leu Glu
                165             170             175

Asp Ile Ala His Val Arg Gln Arg Leu Asp Asp Glu Ala Arg Gln Arg
            180             185             190

Glu Glu Ala Glu Ala Ala Arg Ala Leu Ala Arg Phe Ala Gln Glu
    195             200             205

Ala Glu Ala Ala Arg Val Asp Leu Gln Lys Lys Ala Gln Ala Leu Gln
    210             215             220

Glu Glu Cys Gly Tyr Leu Arg Arg His His Gln Glu Val Gly Glu
225             230             235             240

Leu Leu Gly Gln Ile Gln Gly Ser Gly Ala Gln Ala Gln Met Gln
                245             250             255

Ala Glu Thr Arg Asp Ala Leu Lys Cys Asp Val Thr Ser Ala Leu Arg
            260             265             270

Glu Ile Arg Ala Gln Leu Glu Gly His Ala Val Gln Ser Thr Leu Gln
            275             280             285

Ser Glu Glu Trp Phe Arg Val Arg Leu Asp Arg Leu Ser Glu Ala Ala
    290             295             300

Lys Val Asn Thr Asp Ala Met Arg Ser Ala Gln Glu Glu Ile Thr Glu
305             310             315             320

Tyr Arg Arg Gln Leu Gln Ala Arg Thr Thr Glu Leu Glu Ala Leu Lys
            325             330             335

Ser Thr Lys Asp Ser Leu Glu Arg Gln Arg Ser Glu Leu Glu Asp Arg
            340             345             350

His Gln Ala Asp Ile Ala Ser Tyr Gln Glu Ala Ile Gln Gln Leu Asp
            355             360             365

Ala Glu Leu Arg Asn Thr Lys Trp Glu Met Ala Ala Gln Leu Arg Glu
    370             375             380

Tyr Gln Asp Leu Leu Asn Val Lys Met Ala Leu Asp Ile Glu Ile Ala
385             390             395             400

Ala Tyr Arg Lys Leu Leu Glu Gly Glu Glu Cys Arg Ile Gly Phe Gly
            405             410             415

Pro Ile Pro Phe Ser Leu Pro Glu Gly Leu Pro Lys Ile Pro Ser Val
            420             425             430

Ser Thr His Ile Lys Val Lys Ser Glu Glu Lys Ile Lys Val Val Glu
            435             440             445

Lys Ser Glu Lys Glu Thr Val Ile Val Glu Glu Gln Thr Glu Glu Thr
450             455             460

Gln Val Thr Glu Glu Val Thr Glu Glu Glu Glu Lys Glu Ala Lys Glu
```

```
            465                 470                 475                 480
        Glu Glu Gly Lys Glu Glu Gly Gly Glu Glu Glu Ala Glu Gly
                        485                 490                 495

Gly Glu Glu Glu Thr Lys Ser Pro Pro Ala Glu Glu Ala Ala Ser Pro
                        500                 505                 510

Glu Lys Glu Ala Lys Ser Pro Val Lys Glu Glu Ala Lys Ser Pro Ala
                        515                 520                 525

Glu Ala Lys Ser Pro Glu Lys Glu Ala Lys Ser Pro Ala Glu Val
                    530                 535                 540

Lys Ser Pro Glu Lys Ala Lys Ser Pro Ala Lys Glu Glu Ala Lys Ser
        545                 550                 555                 560

Pro Pro Glu Ala Lys Ser Pro Glu Lys Glu Glu Ala Lys Ser Pro Ala
                        565                 570                 575

Glu Val Lys Ser Pro Glu Lys Ala Lys Ser Pro Ala Lys Glu Glu Ala
                        580                 585                 590

Lys Ser Pro Ala Glu Ala Lys Ser Pro Glu Lys Ala Lys Ser Pro Val
                        595                 600                 605

Lys Glu Glu Ala Lys Ser Pro Ala Glu Ala Lys Ser Pro Val Lys Glu
                    610                 615                 620

Glu Ala Lys Ser Pro Ala Glu Val Lys Ser Pro Glu Lys Ala Lys Ser
        625                 630                 635                 640

Pro Thr Lys Glu Glu Ala Lys Ser Pro Glu Lys Ala Lys Ser Pro Glu
                        645                 650                 655

Lys Glu Glu Ala Lys Ser Pro Glu Lys Ala Lys Ser Pro Val Lys Ala
                        660                 665                 670

Glu Ala Lys Ser Pro Glu Lys Ala Lys Ser Pro Val Lys Ala Glu Ala
                    675                 680                 685

Lys Ser Pro Glu Lys Ala Lys Ser Pro Val Lys Glu Glu Ala Lys Ser
                    690                 695                 700

Pro Glu Lys Ala Lys Ser Pro Val Lys Glu Glu Ala Lys Ser Pro Glu
        705                 710                 715                 720

Lys Ala Lys Ser Pro Val Lys Glu Glu Ala Lys Thr Pro Glu Lys Ala
                        725                 730                 735

Lys Ser Pro Val Lys Glu Glu Ala Lys Ser Pro Glu Lys Ala Lys Ser
                        740                 745                 750

Pro Glu Lys Ala Lys Thr Leu Asp Val Lys Ser Pro Glu Ala Lys Thr
                        755                 760                 765

Pro Ala Lys Glu Glu Ala Arg Ser Pro Ala Asp Lys Phe Pro Glu Lys
                        770                 775                 780

Ala Lys Ser Pro Val Lys Glu Val Lys Ser Pro Glu Lys Ala Lys
        785                 790                 795                 800

Ser Pro Leu Lys Glu Asp Ala Lys Ala Pro Glu Lys Glu Ile Pro Lys
                        805                 810                 815

Lys Glu Glu Val Lys Ser Pro Val Lys Glu Glu Glu Lys Pro Gln Glu
                        820                 825                 830

Val Lys Val Lys Glu Pro Pro Lys Lys Ala Glu Glu Lys Ala Pro
                    835                 840                 845

Ala Thr Pro Lys Thr Glu Glu Lys Lys Asp Ser Lys Lys Glu Glu Ala
                        850                 855                 860

Pro Lys Lys Glu Ala Pro Lys Pro Lys Val Glu Glu Lys Lys Glu Pro
        865                 870                 875                 880

Ala Val Glu Lys Pro Lys Glu Ser Lys Val Glu Ala Lys Lys Glu Glu
                        885                 890                 895
```

```
Ala Glu Asp Lys Lys Val Pro Thr Pro Glu Lys Glu Pro Ala
                900                 905                 910

Lys Val Glu Val Lys Glu Asp Ala Lys Pro Lys Glu Thr Glu Val
    915                 920                 925

Ala Lys Lys Glu Pro Asp Asp Ala Lys Ala Lys Glu Pro Ser Lys Pro
930                 935                 940

Ala Glu Lys Lys Glu Ala Ala Pro Glu Lys Lys Asp Thr Lys Glu Glu
945                 950                 955                 960

Lys Ala Lys Lys Pro Glu Glu Lys Pro Lys Thr Glu Ala Lys Ala Lys
            965                 970                 975

Glu Asp Asp Lys Thr Leu Ser Lys Glu Pro Ser Lys Pro Lys Ala Glu
            980                 985                 990

Lys Ala Glu Lys Ser Ser Ser Thr Asp Gln Lys Asp Ser Lys Pro Pro
    995                 1000                1005

Glu Lys Ala Thr Glu Asp Lys Ala Ala Lys Gly Lys
    1010                1015                1020

<210> SEQ ID NO 4
<211> LENGTH: 916
<212> TYPE: PRT
<213> ORGANISM: Homo sapiens

<400> SEQUENCE: 4

Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
            20                  25                  30

Ser Gly Phe Arg Ser Gln Ser Trp Ser Arg Gly Ser Pro Ser Thr Val
        35                  40                  45

Ser Ser Ser Tyr Lys Arg Ser Met Leu Ala Pro Arg Leu Ala Tyr Ser
    50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Pro Gly Gly Asp Tyr Lys Leu
                85                  90                  95

Ser Arg Ser Asn Glu Lys Glu Gln Leu Gln Gly Leu Asn Asp Arg Phe
            100                 105                 110

Ala Gly Tyr Ile Glu Lys Val His Tyr Leu Glu Gln Gln Asn Lys Glu
        115                 120                 125

Ile Glu Ala Glu Ile Gln Ala Leu Arg Gln Lys Gln Ala Ser His Ala
130                 135                 140

Gln Leu Gly Asp Ala Tyr Asp Gln Glu Ile Arg Glu Leu Arg Ala Thr
145                 150                 155                 160

Leu Glu Met Val Asn His Glu Lys Ala Gln Val Gln Leu Asp Ser Asp
                165                 170                 175

His Leu Glu Glu Asp Ile His Arg Leu Lys Glu Arg Phe Glu Glu Glu
            180                 185                 190

Ala Arg Leu Arg Asp Asp Thr Glu Ala Ala Ile Arg Ala Leu Arg Lys
        195                 200                 205

Asp Ile Glu Glu Ala Ser Leu Val Lys Val Glu Leu Asp Lys Lys Val
210                 215                 220

Gln Ser Leu Gln Asp Glu Val Ala Phe Leu Arg Ser Asn His Glu Glu
225                 230                 235                 240

Glu Val Ala Asp Leu Leu Ala Gln Ile Gln Ala Ser His Ile Thr Val
```

```
                         245                 250                 255
        Glu Arg Lys Asp Tyr Leu Lys Thr Asp Ile Ser Thr Ala Leu Lys Glu
                        260                 265                 270

Ile Arg Ser Gln Leu Glu Ser His Ser Asp Gln Asn Met His Gln Ala
                        275                 280                 285

Glu Glu Trp Phe Lys Cys Arg Tyr Ala Lys Leu Thr Glu Ala Ala Glu
                        290                 295                 300

Gln Asn Lys Glu Ala Ile Arg Ser Ala Lys Glu Glu Ile Ala Glu Tyr
        305                 310                 315                 320

Arg Arg Gln Leu Gln Ser Lys Ser Ile Glu Leu Glu Ser Val Arg Gly
                        325                 330                 335

Thr Lys Glu Ser Leu Glu Arg Gln Leu Ser Asp Ile Glu Glu Arg His
                        340                 345                 350

Asn His Asp Leu Ser Ser Tyr Gln Asp Thr Ile Gln Gln Leu Glu Asn
                        355                 360                 365

Glu Leu Arg Gly Thr Lys Trp Glu Met Ala Arg His Leu Arg Glu Tyr
                        370                 375                 380

Gln Asp Leu Leu Asn Val Lys Met Ala Leu Asp Ile Glu Ile Ala Ala
        385                 390                 395                 400

Tyr Arg Lys Leu Leu Glu Gly Glu Glu Thr Arg Phe Ser Thr Phe Ala
                        405                 410                 415

Gly Ser Ile Thr Gly Pro Leu Tyr Thr His Arg Pro Pro Ile Thr Ile
                        420                 425                 430

Ser Ser Lys Ile Gln Lys Pro Lys Val Glu Ala Pro Lys Leu Lys Val
                        435                 440                 445

Gln His Lys Phe Val Glu Glu Ile Ile Glu Glu Thr Lys Val Glu Asp
                        450                 455                 460

Glu Lys Ser Glu Met Glu Glu Ala Leu Thr Ala Ile Thr Glu Glu Leu
        465                 470                 475                 480

Ala Val Ser Met Lys Glu Glu Lys Lys Glu Ala Ala Glu Glu Lys Glu
                        485                 490                 495

Glu Glu Pro Glu Ala Glu Glu Glu Val Ala Ala Lys Lys Ser Pro
                        500                 505                 510

Val Lys Ala Thr Ala Pro Glu Val Lys Glu Glu Glu Gly Glu Lys Glu
                        515                 520                 525

Glu Glu Glu Gly Gln Glu Glu Glu Glu Asp Glu Gly Ala Lys
                        530                 535                 540

Ser Asp Gln Ala Glu Glu Gly Gly Ser Glu Lys Glu Gly Ser Ser Glu
        545                 550                 555                 560

Lys Glu Glu Gly Glu Gln Glu Glu Gly Glu Thr Glu Ala Glu Ala Glu
                        565                 570                 575

Gly Glu Glu Ala Glu Ala Lys Glu Glu Lys Lys Val Glu Glu Lys Ser
                        580                 585                 590

Glu Glu Val Ala Thr Lys Glu Glu Leu Val Ala Asp Ala Lys Val Glu
                        595                 600                 605

Lys Pro Glu Lys Ala Lys Ser Pro Val Pro Lys Ser Pro Val Glu Glu
                        610                 615                 620

Lys Gly Lys Ser Pro Val Pro Lys Ser Pro Val Glu Glu Lys Gly Lys
        625                 630                 635                 640

Ser Pro Val Pro Lys Ser Pro Val Glu Glu Lys Gly Lys Ser Pro Val
                        645                 650                 655

Pro Lys Ser Pro Val Glu Glu Lys Gly Lys Ser Pro Val Ser Lys Ser
                        660                 665                 670
```

-continued

Pro Val Glu Glu Lys Ala Lys Ser Pro Val Pro Lys Ser Pro Val Glu
                675                 680                 685

Glu Ala Lys Ser Lys Ala Glu Val Gly Lys Gly Glu Gln Lys Glu Glu
        690                 695                 700

Glu Glu Lys Glu Val Lys Glu Ala Pro Lys Glu Glu Lys Val Glu Lys
705                 710                 715                 720

Lys Glu Glu Lys Pro Lys Asp Val Pro Glu Lys Lys Ala Glu Ser
                725                 730                 735

Pro Val Lys Glu Glu Ala Val Ala Glu Val Val Thr Ile Thr Lys Ser
                740                 745                 750

Val Lys Val His Leu Glu Lys Glu Thr Lys Glu Glu Gly Lys Pro Leu
        755                 760                 765

Gln Gln Glu Lys Glu Lys Glu Lys Ala Gly Gly Glu Gly Gly Ser Glu
        770                 775                 780

Glu Glu Gly Ser Asp Lys Gly Ala Lys Gly Ser Arg Lys Glu Asp Ile
785                 790                 795                 800

Ala Val Asn Gly Glu Val Gly Lys Glu Val Glu Gln Glu Thr
                805                 810                 815

Lys Glu Lys Gly Ser Gly Arg Glu Glu Glu Lys Gly Val Val Thr Asn
        820                 825                 830

Gly Leu Asp Leu Ser Pro Ala Asp Glu Lys Lys Gly Gly Asp Lys Ser
        835                 840                 845

Glu Glu Lys Val Val Val Thr Lys Thr Val Glu Lys Ile Thr Ser Glu
850                 855                 860

Gly Gly Asp Gly Ala Thr Lys Tyr Ile Thr Lys Ser Val Thr Val Thr
865                 870                 875                 880

Gln Lys Val Glu Glu His Glu Glu Thr Phe Glu Glu Lys Leu Val Ser
        885                 890                 895

Thr Lys Lys Val Glu Lys Val Thr Ser His Ala Ile Val Lys Glu Val
                900                 905                 910

Thr Gln Ser Asp
        915

<210> SEQ ID NO 5
<211> LENGTH: 540
<212> TYPE: PRT
<213> ORGANISM: Homo sapiens

<400> SEQUENCE: 5

Met Ala Arg His Leu Arg Glu Tyr Gln Asp Leu Leu Asn Val Lys Met
1               5                   10                  15

Ala Leu Asp Ile Glu Ile Ala Ala Tyr Arg Lys Leu Leu Glu Gly Glu
                20                  25                  30

Glu Thr Arg Phe Ser Thr Phe Ala Gly Ser Ile Thr Gly Pro Leu Tyr
            35                  40                  45

Thr His Arg Pro Pro Ile Thr Ile Ser Ser Lys Ile Gln Lys Pro Lys
        50                  55                  60

Val Glu Ala Pro Lys Leu Lys Val Gln His Lys Phe Val Glu Glu Ile
65                  70                  75                  80

Ile Glu Glu Thr Lys Val Glu Asp Glu Lys Ser Glu Met Glu Glu Ala
                85                  90                  95

Leu Thr Ala Ile Thr Glu Glu Leu Ala Val Ser Met Lys Glu Glu Lys
                100                 105                 110

Lys Glu Ala Ala Glu Glu Lys Glu Glu Glu Pro Glu Ala Glu Glu Glu

```
            115                 120                 125
Glu Val Ala Ala Lys Lys Ser Pro Val Lys Ala Thr Ala Pro Glu Val
130                 135                 140
Lys Glu Glu Glu Gly Glu Lys Glu Glu Glu Glu Gln Glu Glu Glu
145                 150                 155                 160
Glu Glu Glu Asp Glu Gly Ala Lys Ser Asp Gln Ala Glu Glu Gly Gly
                165                 170                 175
Ser Glu Lys Glu Gly Ser Ser Glu Lys Glu Gly Gln Glu Glu
                180                 185                 190
Gly Glu Thr Glu Ala Glu Ala Glu Gly Glu Glu Ala Glu Ala Lys Glu
            195                 200                 205
Glu Lys Lys Val Glu Glu Lys Ser Glu Glu Val Ala Thr Lys Glu Glu
        210                 215                 220
Leu Val Ala Asp Ala Lys Val Glu Lys Pro Lys Ala Lys Ser Pro
225                 230                 235                 240
Val Pro Lys Ser Pro Val Glu Glu Lys Gly Lys Ser Pro Val Pro Lys
                245                 250                 255
Ser Pro Val Glu Glu Lys Gly Lys Ser Pro Val Pro Lys Ser Pro Val
                260                 265                 270
Glu Glu Lys Gly Lys Ser Pro Val Pro Lys Ser Pro Val Glu Glu Lys
            275                 280                 285
Gly Lys Ser Pro Val Ser Lys Ser Pro Val Glu Glu Lys Ala Lys Ser
        290                 295                 300
Pro Val Pro Lys Ser Pro Val Glu Glu Ala Lys Ser Lys Ala Glu Val
305                 310                 315                 320
Gly Lys Gly Glu Gln Lys Glu Glu Glu Lys Glu Val Lys Glu Ala
                325                 330                 335
Pro Lys Glu Glu Lys Val Glu Lys Lys Glu Glu Lys Pro Lys Asp Val
                340                 345                 350
Pro Glu Lys Lys Ala Glu Ser Pro Val Lys Glu Glu Ala Val Ala
                355                 360                 365
Glu Val Val Thr Ile Thr Lys Ser Val Lys Val His Leu Glu Lys Glu
        370                 375                 380
Thr Lys Glu Glu Gly Lys Pro Leu Gln Gln Glu Lys Glu Lys Glu Lys
385                 390                 395                 400
Ala Gly Gly Glu Gly Gly Ser Glu Glu Glu Gly Ser Asp Lys Gly Ala
                405                 410                 415
Lys Gly Ser Arg Lys Glu Asp Ile Ala Val Asn Gly Glu Val Glu Gly
                420                 425                 430
Lys Glu Glu Val Glu Gln Glu Thr Lys Glu Lys Gly Ser Gly Arg Glu
            435                 440                 445
Glu Glu Lys Gly Val Val Thr Asn Gly Leu Asp Leu Ser Pro Ala Asp
        450                 455                 460
Glu Lys Lys Gly Gly Asp Lys Ser Glu Glu Lys Val Val Thr Lys
465                 470                 475                 480
Thr Val Glu Lys Ile Thr Ser Glu Gly Asp Gly Ala Thr Lys Tyr
                485                 490                 495
Ile Thr Lys Ser Val Thr Val Thr Gln Lys Val Glu Glu His Glu Glu
            500                 505                 510
Thr Phe Glu Glu Lys Leu Val Ser Thr Lys Lys Val Glu Lys Val Thr
        515                 520                 525
Ser His Ala Ile Val Lys Glu Val Thr Gln Ser Asp
        530                 535                 540
```

<210> SEQ ID NO 6
<211> LENGTH: 499
<212> TYPE: PRT
<213> ORGANISM: Homo sapiens

<400> SEQUENCE: 6

```
Met Ser Phe Gly Ser Glu His Tyr Leu Cys Ser Ser Ser Tyr Arg
1               5                   10                  15

Lys Val Phe Gly Asp Gly Ser Arg Leu Ser Ala Arg Leu Ser Gly Ala
                20                  25                  30

Gly Gly Ala Gly Gly Phe Arg Ser Gln Ser Leu Ser Arg Ser Asn Val
            35                  40                  45

Ala Ser Ser Ala Ala Cys Ser Ser Ala Ser Leu Gly Leu Gly Leu
50                  55                  60

Ala Tyr Arg Arg Pro Pro Ala Ser Asp Gly Leu Asp Leu Ser Gln Ala
65                  70                  75                  80

Ala Ala Arg Thr Asn Glu Tyr Lys Ile Ile Arg Thr Asn Glu Lys Glu
                85                  90                  95

Gln Leu Gln Gly Leu Asn Asp Arg Phe Ala Val Phe Ile Glu Lys Val
            100                 105                 110

His Gln Leu Glu Thr Gln Asn Arg Ala Leu Glu Ala Glu Leu Ala Ala
        115                 120                 125

Leu Arg Gln Arg His Ala Glu Pro Ser Arg Val Gly Glu Leu Phe Gln
130                 135                 140

Arg Glu Leu Arg Asp Leu Arg Ala Gln Leu Glu Glu Ala Ser Ser Ala
145                 150                 155                 160

Arg Ser Gln Ala Leu Leu Glu Arg Asp Gly Leu Ala Glu Glu Val Gln
                165                 170                 175

Arg Leu Arg Ala Arg Cys Glu Glu Glu Ser Arg Gly Arg Glu Gly Ala
            180                 185                 190

Glu Arg Ala Leu Lys Ala Gln Gln Arg Asp Val Asp Gly Ala Thr Leu
        195                 200                 205

Ala Arg Leu Asp Leu Glu Lys Lys Val Glu Ser Leu Leu Asp Glu Leu
210                 215                 220

Ala Phe Val Arg Gln Val His Asp Glu Glu Val Ala Glu Leu Leu Ala
225                 230                 235                 240

Thr Leu Gln Ala Ser Ser Gln Ala Ala Ala Glu Val Asp Val Thr Val
                245                 250                 255

Ala Lys Pro Asp Leu Thr Ser Ala Leu Arg Glu Ile Arg Ala Gln Tyr
            260                 265                 270

Glu Ser Leu Ala Ala Lys Asn Leu Gln Ser Ala Glu Glu Trp Tyr Lys
        275                 280                 285

Ser Lys Phe Ala Asn Leu Asn Glu Gln Ala Ala Arg Ser Thr Glu Ala
290                 295                 300

Ile Arg Ala Ser Arg Glu Glu Ile His Glu Tyr Arg Arg Gln Leu Gln
305                 310                 315                 320

Ala Arg Thr Ile Glu Ile Glu Gly Leu Arg Gly Ala Asn Glu Ser Leu
                325                 330                 335

Glu Arg Gln Ile Leu Glu Leu Glu Arg His Ser Ala Glu Val Ala
            340                 345                 350

Gly Tyr Gln Asp Ser Ile Gly Gln Leu Glu Asn Asp Leu Arg Asn Thr
        355                 360                 365

Lys Ser Glu Met Ala Arg His Leu Arg Glu Tyr Gln Asp Leu Leu Asn
```

```
            370                 375                 380
Val Lys Met Ala Leu Asp Ile Glu Ile Ala Ala Tyr Arg Lys Leu Leu
385                 390                 395                 400

Glu Gly Glu Glu Thr Arg Phe Ser Thr Ser Gly Leu Ser Ile Ser Gly
                405                 410                 415

Leu Asn Pro Leu Pro Asn Pro Ser Tyr Leu Leu Pro Pro Arg Ile Leu
                420                 425                 430

Ser Ala Thr Thr Ser Lys Val Ser Ser Thr Gly Leu Ser Leu Lys Lys
                435                 440                 445

Glu Glu Glu Glu Glu Ala Ser Lys Val Ala Ser Lys Lys Thr Ser
450                 455                 460

Gln Ile Gly Glu Ser Phe Glu Glu Ile Leu Glu Glu Thr Val Ile Ser
465                 470                 475                 480

Thr Lys Lys Thr Glu Lys Ser Asn Ile Glu Thr Thr Ile Ser Ser
                485                 490                 495

Gln Lys Ile
```

<210> SEQ ID NO 7
<211> LENGTH: 470
<212> TYPE: PRT
<213> ORGANISM: Homo sapiens

<400> SEQUENCE: 7

```
Met Ser His His Pro Ser Gly Leu Arg Ala Gly Phe Ser Ser Thr Ser
1               5                   10                  15

Tyr Arg Arg Thr Phe Gly Pro Pro Ser Leu Ser Pro Gly Ala Phe
                20                  25                  30

Ser Tyr Ser Ser Ser Arg Phe Ser Ser Arg Leu Leu Gly Ser
            35                  40                  45

Ala Ser Pro Ser Ser Ser Val Arg Leu Gly Ser Phe Arg Ser Pro Arg
50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
            115                 120                 125

Leu Ser Gln Ala Arg Gly Gln Glu Pro Ala Arg Ala Asp Gln Leu Cys
130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Thr Arg Lys Arg Glu Asp
                180                 185                 190

Ala Glu His Asn Leu Val Leu Phe Arg Lys Asp Val Asp Asp Ala Thr
            195                 200                 205

Leu Ser Arg Leu Glu Leu Glu Arg Lys Ile Glu Ser Leu Met Asp Glu
210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
```

```
                245                 250                 255
Val Lys Pro Glu Leu Thr Ala Ala Leu Arg Asp Ile Arg Ala Gln Tyr
            260                 265                 270
Glu Ser Ile Ala Ala Lys Asn Leu Gln Glu Ala Glu Glu Trp Tyr Lys
        275                 280                 285
Ser Lys Tyr Ala Asp Leu Ser Asp Ala Ala Asn Arg Asn His Glu Ala
    290                 295                 300
Leu Arg Gln Ala Lys Gln Glu Met Asn Glu Ser Arg Arg Gln Ile Gln
305                 310                 315                 320
Ser Leu Thr Cys Glu Val Asp Gly Leu Arg Gly Thr Asn Glu Ala Leu
            325                 330                 335
Leu Arg Gln Leu Arg Glu Leu Glu Glu Gln Phe Ala Leu Glu Ala Gly
        340                 345                 350
Gly Tyr Gln Ala Gly Ala Ala Arg Leu Glu Glu Glu Leu Arg Gln Leu
    355                 360                 365
Lys Glu Glu Met Ala Arg His Leu Arg Glu Tyr Gln Glu Leu Leu Asn
370                 375                 380
Val Lys Met Ala Leu Asp Ile Glu Ile Ala Thr Tyr Arg Lys Leu Leu
385                 390                 395                 400
Glu Gly Glu Glu Ser Arg Ile Ser Val Pro Val His Ser Phe Ala Ser
            405                 410                 415
Leu Asn Ile Lys Thr Thr Val Pro Glu Val Glu Pro Pro Gln Asp Ser
        420                 425                 430
His Ser Arg Lys Thr Val Leu Ile Lys Thr Ile Glu Thr Arg Asn Gly
    435                 440                 445
Glu Val Val Thr Glu Ser Gln Lys Glu Gln Arg Ser Glu Leu Asp Lys
    450                 455                 460
Ser Ser Ala His Ser Tyr
465                 470

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
caggatacat ttctacagct                                              20

<210> SEQ ID NO 9
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ttaatgttta tcaggat                                                 17

<210> SEQ ID NO 10
<211> LENGTH: 17
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 10
agtgtttaat gtttatc                                                   17

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ccgtcgccct tcagcacgca                                                20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
ccttccctga aggttcctcc                                                20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
cctataggac tatccaggaa                                                20
```